(12) United States Patent
Armbruster et al.

(10) Patent No.: US 10,485,904 B2
(45) Date of Patent: Nov. 26, 2019

(54) DRUG ELUTING INSERT FOR IMPLANTABLE BODY

(71) Applicant: DePuy Synthes Products, Inc., Raynham, MA (US)

(72) Inventors: David Armbruster, West Chester, PA (US); Katlin Adlon Lumme, Marietta, GA (US); Jeffrey Chomyn, Maurrieta, CA (US); Aaron Yu, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 102 days.

(21) Appl. No.: 15/240,210

(22) Filed: Aug. 18, 2016

(65) Prior Publication Data

US 2016/0354523 A1 Dec. 8, 2016

Related U.S. Application Data

(63) Continuation of application No. 13/767,061, filed on Feb. 14, 2013, now Pat. No. 9,440,009.
(Continued)

(51) Int. Cl.
*A61B 17/72* (2006.01)
*A61L 31/16* (2006.01)
(Continued)

(52) U.S. Cl.
CPC .............. *A61L 31/16* (2013.01); *A61B 17/72* (2013.01); *A61B 17/80* (2013.01); *A61B 17/84* (2013.01);
(Continued)

(58) Field of Classification Search
CPC ... A61B 17/864; A61B 17/72; A61B 17/7216; A61B 17/7233; A61B 17/66; A61B 17/8866; A61B 17/8869
(Continued)

(56) References Cited

U.S. PATENT DOCUMENTS 4,190,044 A    2/1980  Wood
5,034,012 A *  7/1991  Frigg ..................... A61B 17/72
                                                  606/104

(Continued)

FOREIGN PATENT DOCUMENTS

EP    0520177    12/1992
EP    0922437     6/1999
(Continued)

OTHER PUBLICATIONS

International Patent Application No. PCT/US2013: International Search Report dated May 8, 2013, 13 pages.

*Primary Examiner* — Eduardo C Robert
*Assistant Examiner* — Christina NegrelliRodriguez
(74) *Attorney, Agent, or Firm* — BakerHostetler

(57) ABSTRACT

The present application discloses embodiments related to an implant and a method of forming an implant configured to treat a fractured bone. The implant can include a body having a proximal end, a distal end, and an outer surface extending from the proximal end to the distal end, wherein the body defines a central axis extending from the proximal end to the distal end; and a high tensile strand positioned adjacent the body such that at least a portion of the strand extends at least partially along the outer surface of the body in a direction substantially parallel with the central axis, and wherein the strand is loaded with an active agent.

21 Claims, 16 Drawing Sheets

Related U.S. Application Data

(60) Provisional application No. 61/599,568, filed on Feb. 16, 2012.

(51) Int. Cl.
  A61B 17/80 (2006.01)
  A61B 17/84 (2006.01)
  *A61B 17/00* (2006.01)
  *A61B 17/56* (2006.01)
  *A61F 2/30* (2006.01)

(52) U.S. Cl.
  CPC ............... *A61B 2017/00004* (2013.01); *A61B 2017/561* (2013.01); *A61F 2002/30677* (2013.01); *A61L 2300/406* (2013.01); *A61L 2430/02* (2013.01); *Y10T 29/49826* (2015.01)

(58) Field of Classification Search
  USPC .............. 606/304, 62–68, 104, 105; 604/264
  See application file for complete search history.

(56) References Cited

U.S. PATENT DOCUMENTS

| | | |
|---|---|---|
| 5,458,653 A | 10/1995 | Davidson |
| 5,618,286 A | 4/1997 | Brinker |
| 5,879,352 A * | 3/1999 | Filoso ................ A61B 17/7013 606/60 |
| 6,231,576 B1 * | 5/2001 | Frigg ................ A61B 17/7208 606/60 |
| 6,596,296 B1 | 7/2003 | Nelson et al. |
| 7,033,603 B2 | 4/2006 | Nelson et al. |
| 2002/0055701 A1 | 5/2002 | Fischell |
| 2006/0276841 A1 | 12/2006 | Barbieri et al. |
| 2007/0213725 A1 | 9/2007 | Hack |
| 2007/0288016 A1 | 12/2007 | Halder |
| 2008/0306511 A1 | 12/2008 | Cooper |
| 2010/0278891 A1 | 11/2010 | Ringeisen et al. |
| 2011/0054408 A1 | 3/2011 | Wei et al. |
| 2011/0287064 A1 * | 11/2011 | Vogt ....................... A61L 27/28 424/400 |

FOREIGN PATENT DOCUMENTS

| | | |
|---|---|---|
| JP | 03-173555 A | 7/1991 |
| JP | 06-014946 A | 1/1994 |
| JP | 2004-529667 A | 9/2004 |
| JP | 2008-535544 A | 9/2008 |
| JP | 2009-517156 A | 4/2009 |

* cited by examiner

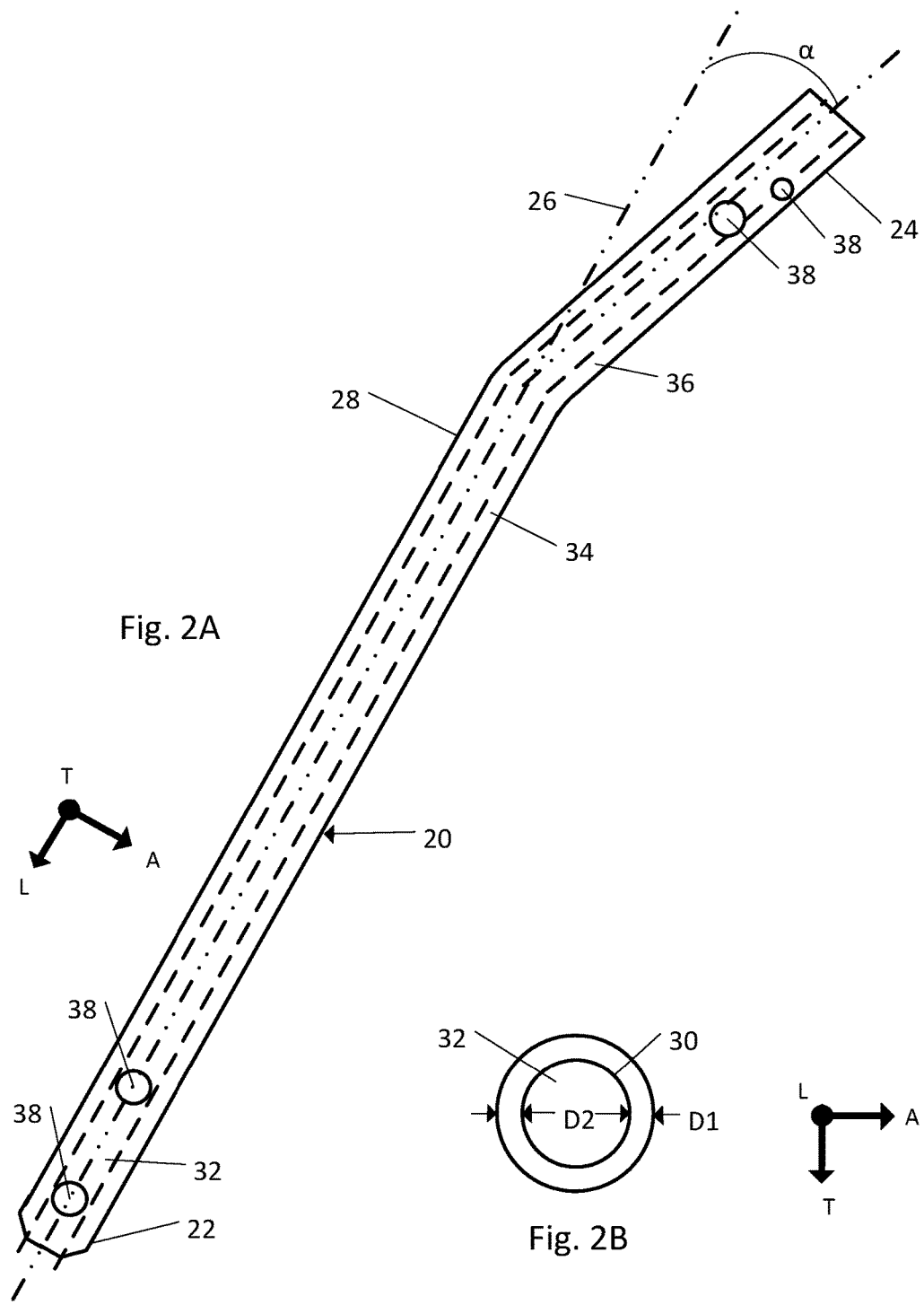

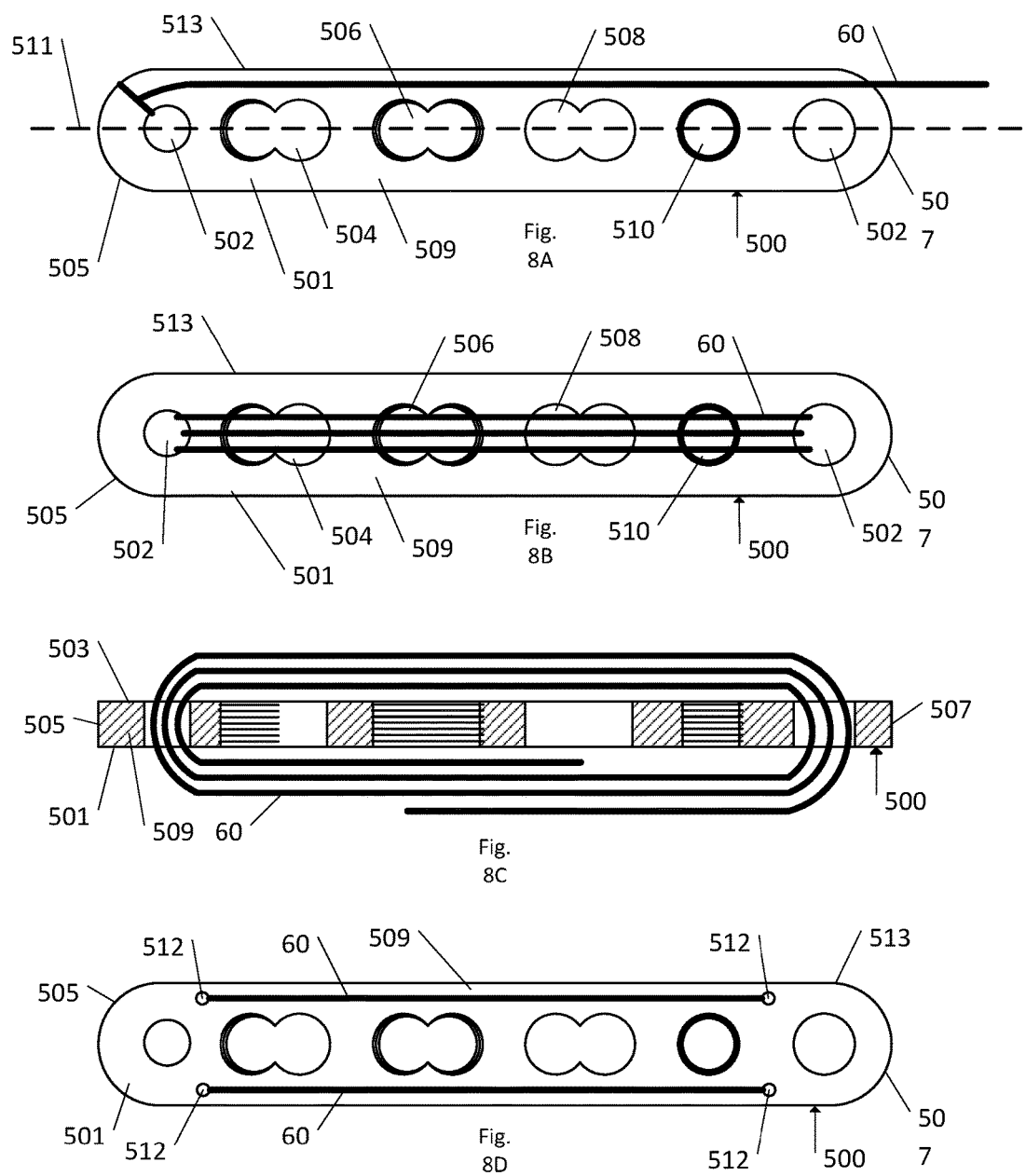

DRUG ELUTING INSERT FOR IMPLANTABLE BODY

CROSS REFERENCE TO RELATED APPLICATIONS

This is a continuation application of U.S. patent application Ser. No. 13/767,061 filed Feb. 14, 2013, which in turn claims benefit to U.S. Provisional Application No. 61/599,568 filed Feb. 16, 2012, herein incorporated by reference in its entirety.

TECHNICAL FIELD

The present disclosure relates generally to orthopedics. More specifically, the present disclosure relates to a system and method for treatment of fractured bone.

BACKGROUND

Orthopedic implant related infection is a potentially catastrophic complication of orthopedic trauma surgery, often requiring extended systemic antibiotic therapy, reoperation, and hardware removal. There is always a risk of infection following any surgical procedure where the protective barrier of the skin is damaged, however when a permanent surgical implant such as an intramedullary nail or osteosynthesis plate remains in the body, the quantity of contaminating bacteria required to cause an infection is significantly reduced. The development of a system and method for local delivery of antibiotics in conjunction with an implant, such as an intramedullary nail, in which the drug delivery mechanism is not permanently attached to the implant, and which can be applied to a variety of different implants of different sizes and in different anatomical locations at the time of surgery could greatly improve the effectiveness of treatment involving orthopedic trauma surgery.

SUMMARY

Various embodiments of an implant configured to treat a fractured bone are disclosed. In one embodiment the implant includes a body having a proximal end, a distal end, and an outer surface extending from the proximal end to the distal end, wherein the body defines a central axis extending from the proximal end to the distal end; and a high tensile strand positioned adjacent the body such that at least a portion of the strand extends at least partially along the outer surface of the body in a direction substantially parallel with the central axis, and wherein the strand is loaded with an active agent.

In another embodiment the implant includes a body having a proximal end and a distal end, wherein the body defines a central axis extending from the proximal end to the distal end; a cap that is affixed to the distal end of the body when the body is implanted; and a high tensile strand received by the cap, wherein the strand is loaded with an active agent.

In another embodiment the implant includes an intramedullary nail having a proximal end, a distal end, an outer surface extending from the proximal end to the distal end, and an inner surface that defines a cannula, the cannula extends in a direction coaxial with the central axis along at least a portion of the implant, and a high tensile strand positioned adjacent the nail such that the strand is at least partially disposed within the cannula and at least partially extends along the outer surface of the nail, and wherein the strand is loaded with an active agent.

In another embodiment the implant includes a bone plate and a high tensile strand. The bone plate includes an outer surface, including, for example, a bottom surface and an opposed top surface; a distal end, an opposed proximal end and a central axis extending from the distal end to the proximal end; and a body that extends from the distal end to the proximal end along a direction parallel to a central axis, the body further extends from the bottom surface to the top surface along a direction perpendicular to the central axis. The high tensile strand is loaded with an active agent and positioned adjacent the bone plate such that the strand is at least partially disposed adjacent the outer surface such that the strand extends along the outer surface in a direction substantially parallel to the central axis.

Methods of forming an implant having an active agent are also disclosed. For example, in one embodiment the method includes the step of affixing a high tensile strand containing an active agent to an implantable body, wherein the implantable body has a proximal end and a distal end, an outer surface extending from the proximal end to the distal end, and wherein the body defines a central axis extending from the proximal end to the distal end, and wherein at least a portion of the affixed strand extends along a portion of the outer surface of the body in a direction substantially parallel with the central axis.

In another embodiment, the method for forming an implant having an active agent includes the steps of affixing a high tensile strand to an implantable body, the high tensile strand containing an active agent, the implantable body has a proximal end, a distal end, and a central axis extending from the proximal end to the distal end, wherein the body includes a cap that is affixed to the distal end of the body when the body is implanted, and wherein the strand is affixed to the cap.

A system configured to form an implant having an active agent is also disclosed. In one embodiment the system includes an implantable body having a proximal end, a distal end, and an outer surface extending from the proximal end to the distal end, wherein the body defines a central axis extending from the proximal end to the distal end, a strand retention mechanism including a cap and a ring, wherein the cap is affixed to the distal end of the body when the strand retention mechanism is implanted and the ring is removably securable to the outer surface of the body, and wherein the ring is slidable along the outer surface of the body from the distal end to the proximal end, and a plurality of high tensile strands configured to be affixed to the cap and removably securable to the ring, wherein at least a portion of each of the plurality of strands extends along a portion of the outer surface of the body in a direction from the cap to the ring, and wherein the strand is loaded with an active agent.

BRIEF DESCRIPTION OF THE DRAWINGS

The foregoing summary, as well as the following detailed description of the preferred embodiments of the application, will be better understood when read in conjunction with the appended drawings. For the purposes of illustrating the surgical instruments and methods of the present application, there is shown in the drawings preferred embodiments. It should be understood, however, that the application is not limited to the specific embodiments and methods disclosed, and reference is made to the claims for that purpose. In the drawings:

FIG. 2A is a side elevation view of the body of the implant illustrated in FIG. 1B;

FIG. 2B is a front view of the body of the implant illustrated in FIG. 1B;

FIG. 8A is a bottom plan view of a strand secured to a bone plate according to one embodiment;

FIG. 8B is a bottom plan view of the strand secured to the bone plate illustrated in FIG. 8A, according to another embodiment;

FIG. 8C is a cross section view of the strand secured to the bone plate illustrated in FIG. 8B;

FIG. 8D is a bottom plan view of the strand secured to the bone plate illustrated in FIG. 8A, according to another embodiment.

DETAILED DESCRIPTION OF ILLUSTRATIVE EMBODIMENTS

Figure 1A:
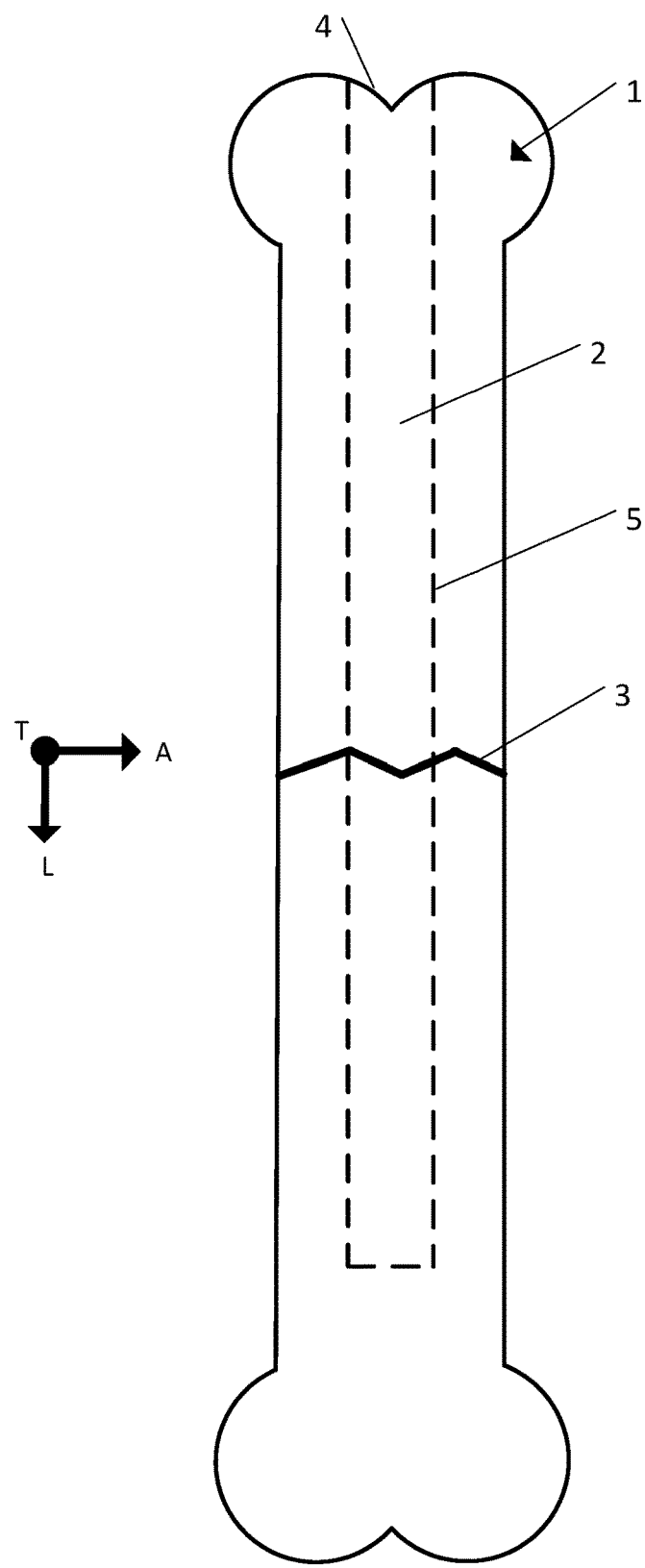
FIG. 1A is a side view of a fractured bone.

Certain terminology is used in the following description for convenience only and is not limiting. The words "distal" and "proximal" refer to directions toward and away from, respectively, the patient's body. The words "front", "rear", "right", "left", "lower" and "upper" designate directions in the drawings to which reference is made. The words, "anterior", "posterior", "superior", "inferior" and related words and/or phrases designate illustrative positions and orientations in the human body to which reference is made and are not meant to be limiting. The terminology includes the above-listed words, derivatives thereof and words of similar import. Additionally, a three dimensional coordinate system is used to describe the positions and orientations of the parts of the implant. The coordinate system includes a longitudinal direction L, a lateral direction A, and a transverse direction T, wherein each of the directions is perpendicular to both of the other two directions.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. Further, reference to values stated in ranges include each and every value within that range. All ranges are inclusive and combinable. Certain features of the invention which are described herein in the context of separate embodiments, may also be provided in combination in a single embodiment. Conversely, various features of the invention that are described in the context of a single embodiment, may also be provided separately or in any subcombination.

Figure 1B:
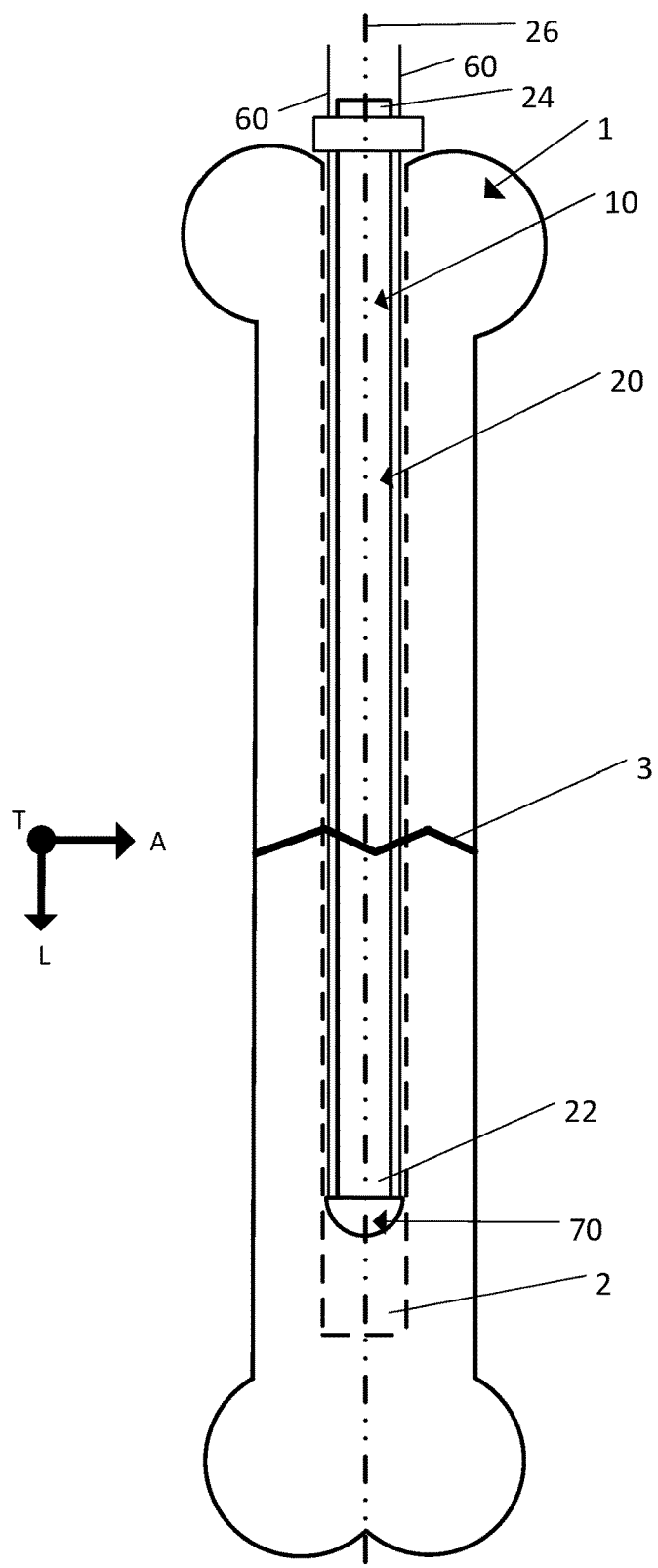
FIG. 1B is a side view of an implant being inserted into the fractured bone illustrated in FIG. 1A, the implant including a body, a strand, and a strand retention mechanism.

Referring to FIGS. 1A and 1B, a fractured bone 1 includes a medullary cavity 2, located within the main shaft of the bone 1, and a fracture 3. The fractured bone 1 can be treated by inserting an implant 10 into the bone 1. The implant 10 can be constructed so as be inserted and positioned within the medullary cavity 2 of the bone 1. The implant 10 can include a body 20, a strand 60, and a strand retention mechanism 70 that secures the strand 60 relative to the body 20. The body 20 can be elongate in the longitudinal direction L, the body extending from a distal end 22 to a proximal end 24 along a central axis 26.

The strand 60 is configured to be secured relative to the body 20 and the strand 60 can be loaded with an active agent. In one embodiment the strand 60 can be a suture, a wire, or any other appropriate thread-like material. In another embodiment the strand 60 can be a thin ribbon of material, such as a strip cut from an extruded film, or a woven or braided textile with a flat geometry. In one embodiment, the active agent can be an antibiotic (such as, for example, gentamicin), the active agent being selected as appropriate to reduce or prevent the chance of infection at the implantation site of the implant 20. The strand retention mechanism 70 is attachable to the body 20 and configured to secure the strand 60 relative to the body 20 such that the active agent is distributed about the implant 10 as desired.

In use, the distal end 22 of the body 20 can be inserted into the medullary cavity 2 of the fractured bone 1 and the body 20 can then be advanced within the medullary cavity 2 until the distal end 22 is positioned on one side of the fracture 3 and the proximal end 24 is positioned on another side of the fracture 3, thus providing fixation for the fractured bone 1 while the fractured bone 1 heals. The use of the implant 10 in the treatment of fractured bone 1 will be described in greater detail below.

Referring to FIGS. 2A and 2B the body 20 has a length that is measured from the distal end 22 to the proximal end 24 along the central axis 26. The body can further include an outer surface 28 that extends from the distal end 22 to the proximal end 24. The outer surface 28 can define an outer diameter D1 of the body 20. The outer diameter D1 of the body 20 can vary such that an implant 10 can be chosen with an appropriate sized outer diameter D1 of the body 20 to treat a particular fractured bone. For example, the outer diameter D1 of a body 20 used to treat a fractured femur may be larger than the outer diameter D1 of a body 20 used to treat a fractured rib. In one embodiment the outer surface 28 of the body 20 can be round, as shown. Alternatively, the outer surface 28 can be tubular or any other shape that is configured to be slidably inserted into the medullary cavity of a bone.

The body 20 can also include an inner surface 30 that defines a cannula (or recess) 32 that extends through at least a portion of the length of the body 20, such that, for example, a passageway is open through the interior of the body 20 from the distal end 22 to the proximal end 24. The inner surface 30 can also define an inner diameter D2. In one embodiment the inner surface 30 can be round, as shown, such that a cross-section of the cannula is a circle. Alternatively, the inner surface 28 can be any other shape as long as an open passageway is provided through the interior of the body 20.

In one embodiment the body 20 can further include a first portion 34 and a second portion 36 directly connected to the first portion 34. The first portion 34 includes the distal end 22 and the second portion 36 includes the proximal end 24. As shown, the first portion 34 can be aligned parallel to the longitudinal direction L and the second portion 36 can be angularly offset (by an angle α) from the first portion 34 with respect to the longitudinal direction L such that the body 20 is bent. The angle α can vary from about 0° (such that the body 20 is not bent) to about 45°. Specifically, the angle α can be about 10° in one embodiment. The body 20 can include a radius at the bend such that body 20 is smooth through the bend. The body 20 can be selected with the appropriate angle α to aid in insertion of the body 20 and also to aid in alignment of the fractured bone when the body 20 has been placed in the medullary cavity 2 of the fractured bone 1. Entry sites for some intramedullary nails are drilled at an angle to avoid joint surfaces or ligaments, the angle α can be selected to correspond to the angle of the entry site.

The body 20 can also define one or more apertures, such as for example locking apertures 38. Each of the one or more locking apertures 38 extends through the body 20 in a direction substantially perpendicular to the central axis 26. The locking apertures 38 can be of various shapes and sizes such that the locking apertures 38 are configured to receive a locking member or a fastener (such as, for example, a nail or a screw). Once the body 20 has been positioned within the fractured bone 1, the locking apertures 38 can each receive a locking member to secure the position of the body 20 relative to the fractured bone. As shown, the locking apertures 38 can be disposed at various locations along the length of the body 20. One or more locking apertures 38 can be located in the distal end 22 and one or more locking apertures 38 can be located in the proximal end 24.

Referring to FIGS. 3A-3D, the strand retention mechanism 70 is configured to secure the strand 60 relative to the body 20 during insertion of the implant 10 into the fractured bone 1. The strand retention mechanism 70 can include a cap or insert 72 (hereinafter referred to as cap) configured to be affixed to the distal end 22 of the body 20 and a ring member 82 that is configured to be received by the outer surface 28 of the body 20. In one embodiment the ring member 82 can be a completed ring, or alternatively the ring member 82 can be a partial ring (for example C-shaped or U-shaped). The cap 72 can be affixed to the distal end 22 of the body 20 in various ways based on the structure of the cap 72. For example, in one embodiment the cap 72 can be disposed at least partially within the cannula 32 of the body 20. In another embodiment the cap 72 can fit over the outer surface 28 of the distal end 22 of the body 20, for instance like a sleeve. In still another embodiment the cap 72 can be affixed to the distal end 22 of the body 20 by using an adhesive. The reference number 72 as used throughout this disclosure refers to the cap or insert in general. Specific embodiments of the cap 72 are described below and each embodiment is identified by an increasing increment of 100 (172, 272, 372, etc.). Any description of the general cap 72 can be combined with any of the specific embodiments of the cap 172, 272, 372, etc.

Figure 3A:
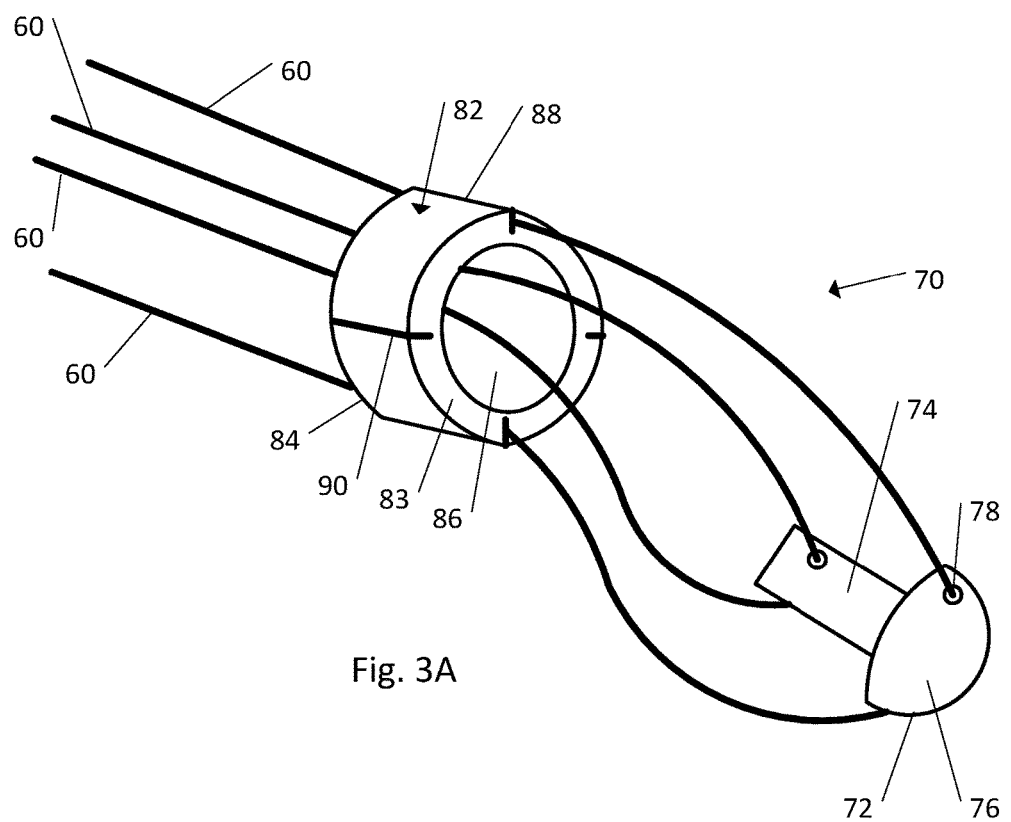
FIG. 3A is a perspective view of the strand and the strand retention mechanism illustrated in FIG. 1B, the strand retention mechanism including a cap and a ring member.
Figure 3B:
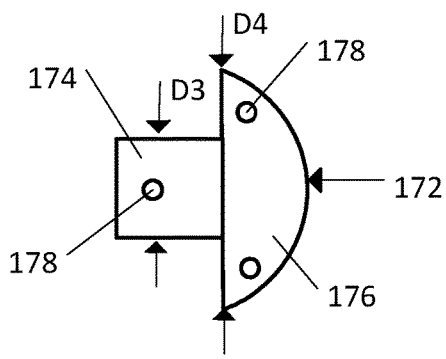
FIG. 3B is a side elevation view of the cap according to another embodiment.

Referring to FIG. 3B, the cap 172 as shown includes a shaft 174 and a tip 176 that is directly coupled to the shaft 174. The shaft 174 defines an outer diameter D3, the outer diameter D3 being configured such that the shaft 174 can be received within the cannula 32 of the body 20. When the cap 172 has been received within the body 20 as described above, the tip 176 can be the leading edge of the implant 10 as the implant 10 is inserted into the medullary cavity 2 of a fractured bone 1. Therefore, in one embodiment the tip 176 can be dome shaped to facilitate insertion of the implant 10 into the bone 1. In one embodiment the tip 176 defines an outer diameter D4 that is greater than the inner diameter D2 of the cannula 32 such that the tip 176 of the cap will not fit entirely within the cannula 32. Additionally, it is preferable that the tip 176 has sufficient mechanical strength to withstand the forces experienced by the implant 10 during insertion into the fractured bone 1, which can often require repeated blows with a hammer. Although the cap 172 has been described above as including a shaft 174 and tip 176, in another embodiment the cap 172 can include any shape such that the cap 172 is configured to be partially received within the cannula 32 of the body 20 and secured relative to the body 20. For example, the cap 172 can be cylindrical, wedge shaped, cork shaped, or plug shaped.

The cap 172 can further include at least one strand securing element 178 that is configured to secure the strand 60 relative to the cap 172 such that as the distal end 22 and the attached cap 172 are advanced into the medullary cavity 2 of the fractured bone 1, the strands 60 are also advanced into the bone 1. In one embodiment the strand securing element 178 can be a bore that the strand 60 is passed through. In another embodiment the strand securing element 178 can include a recess that is crimped closed once the strand has been positioned within the recess. In yet another embodiment the strand securing element 178 can be a notch or hook that receives and secures the strand 60. The strand securing elements 178 can be positioned within the shaft 174 (for strands 60 that are to be disposed within the cannula 32 of the body 20), positioned within the tip 176 (for strands 60 that are to be disposed outside the body 20 and adjacent to the outer surface 28 of the body), or both. In yet another embodiment, the strands 60 are insert molded into an injection molded cap 172 or attached using an adhesive.

Figure 3C:
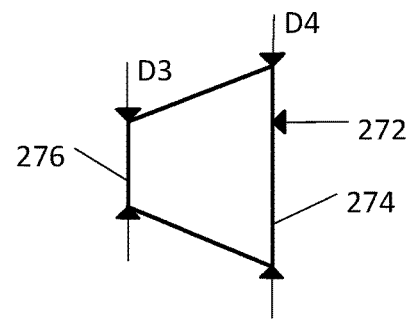
FIG. 3C is a side elevation view of the cap illustrated in FIG. 3A.

Referring to FIG. 3C, in another embodiment the strand retention mechanism 70 can include a cap 272. Cap 272 defines a leading surface 274, a trailing surface 276 and a body 278 that extends from the leading surface 274 to the trailing surface 276. As shown in the illustrated embodiment, the body 278 can have a plug-like or cork-like shape. The cap 272 further defines an outer diameter D3 located near the trailing surface 276, the outer diameter D3 being smaller than the inner diameter D2 of the cannula 32 such that the cap 272 can be at least partially received within the cannula 32 of the body 20. In one embodiment the cap 272 also defines an outer diameter D4 located near the leading surface 274, the outer diameter D4 being greater than the inner diameter D2 of the cannula 32 such that the cap 272 does not fit entirely within the cannula 32. The leading surface 274 can include one or more strand securing elements 78 (see, for example, FIG. 3B) that are configured to secure the one more strands 60 relative to the cap 272. In another embodiment, the strands 60 can be secured to the leading surface 274 in such way, for instance by an adhesive, that a strand securing element is not needed on the cap 272.

The caps 172 and 272 as illustrated in FIGS. 3B and 3C are each configured to be disposed at least partially within the cannula 32 of the body 20. However, other embodiments of the cap 72 are contemplated. In another embodiment the cap 72 can be configured such that the entire cap 72 fits within the cannula 32 of the body 20. This positioning of the cap 72 can decrease the chance of damage to the cap 72 during insertion of the implant 10. In yet another embodiment the cap 72 can be configured such that the entire cap 72 is disposed outside of the cannula 32 of the body 20. As will be described in greater detail below in reference to FIG. 4C, the cap 372 can be a sleeve-like shape that is configured to fit over the outer surface 28 of the distal end 22 of the body 20. The various embodiments of the cap 72 can be constructed from an appropriate material that is selected based on the intended use of the cap 72. For example, the cap 72 can be made from a biodegradable or bioresorbable material, for instance polylactic acid (PLA), polyglycolic acid (PGA), polycaprolactone (PCL), polymethylene carbonate (PMC), polyethylene glycol (PEG) or copolymers of these. A biodegradable or bioresorbable material can be beneficial if it is desired that the cap 72 not be removed after insertion. In another embodiment the cap 72 can be made of a non-biodegradable or non-bioresorbable material, for instance polyethylene, high-density polyethylene (HDPE), ultra-high molecular weight polyethylene (UHMWPE), polypropylene, polyether ether ketone (PEEK), nylon, acrylic, or polyurethane. The cap 72 can also be loaded with active agent by any of the methods described throughout the present disclosure.

Referring to FIGS. 3A and 3D-3F, the ring member 82 can include a front surface 83, an opposed rear surface 84 and a length defined as the distance from the front surface 83 to the rear surface 84. The ring member can also have an inner surface 85 that defines a bore 86 extending through the ring member 82, as shown the bore can be centered on a central axis 87. The bore 86 has a complementary size and shape to the outer surface 28 of the body 20 such that when the central axis 87 of the bore is aligned with the central axis 26 of the body 20, the ring member 82 is slidable along the outer surface 28 of the body 20. In one embodiment, the bore 86 can be a circle with an inner diameter D5, as shown. The inner diameter D5 is slightly larger than the outer diameter D1 of the body 20. The ring member 82 can further include an outer surface 88 that defines an outer diameter D6 of the ring member 82. The outer diameter D6 is greater than the inner diameter D5, such that a thickness is defined between the inner surface 85 and the outer surface 88 measured along a direction from the inner surface 85 to the outer surface 88 and perpendicular to the central axis 87.

Figure 3D:
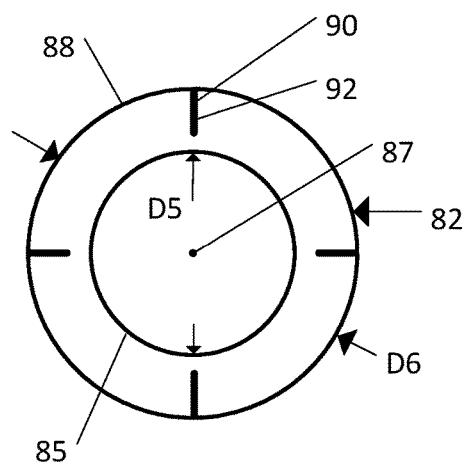
FIG. 3D is a front view of the ring member illustrated in FIG. 3A according to one embodiment.

The ring member 82 can additionally include one or more strand securing elements 90 that are configured to secure the one more strands 60 relative to the outer surface 28 of the body 20 in a desired orientation during insertion of the implant 10 into the medullary cavity 2. As shown in FIG. 3D, the strand securing elements 90 include recesses or notches 92 that extend from the outer surface 88 toward the inner surface 85. The recesses 92 can run the length of the ring member 82 creating a passageway through a portion of the ring member 82, the passageway being configured to slidably receive the strand 60.

Figure 3E:
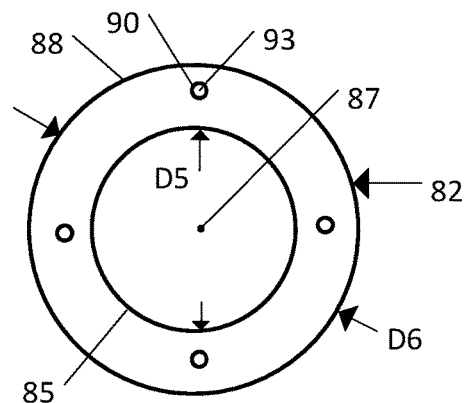
FIG. 3E is a front view of the ring member illustrated in FIG. 3A according to another embodiment.

In another embodiment as shown in FIG. 3E, the strand securing elements 90 can include through bores 93 that extend from the front surface 83 toward the opposed rear surface 84. The bores 93 can run the length of the ring member 82 creating a passageway through a portion of the ring member 82, the passageway being configured to slidably receive the strand 60. The number and positioning of the through bores 93 can vary as desired to accommodate a specific number of strands 60 and retain the strands 60 in desired relative positions to one another. For example, the ring member 82 includes one or more, for instance four, through bores 93 evenly spaced through bores about the circumference of the ring member 82. In another embodiment the through bores 93 can be positioned within the ring member 82 such that the through bores 93 are not evenly spaced from one another.

Figure 3F:
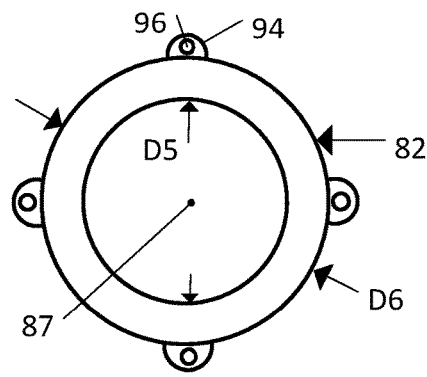
FIG. 3F is a front view of the ring member illustrated in FIG. 3A according to another embodiment.

As shown in FIG. 3F, in another embodiment the strand securing elements 90 include a flange 94 with a hole 96. The hole 96 is configured to slidably receive the strand 60 such that the strand 60 can translate through the hole 96. In yet another embodiment the strand securing element 90 can include any structure that is configured to slidably receive the strand 60 and secure the strand 60 relative to the body 20 during insertion of the implant 10 into the bone 1.

Figure 4A:
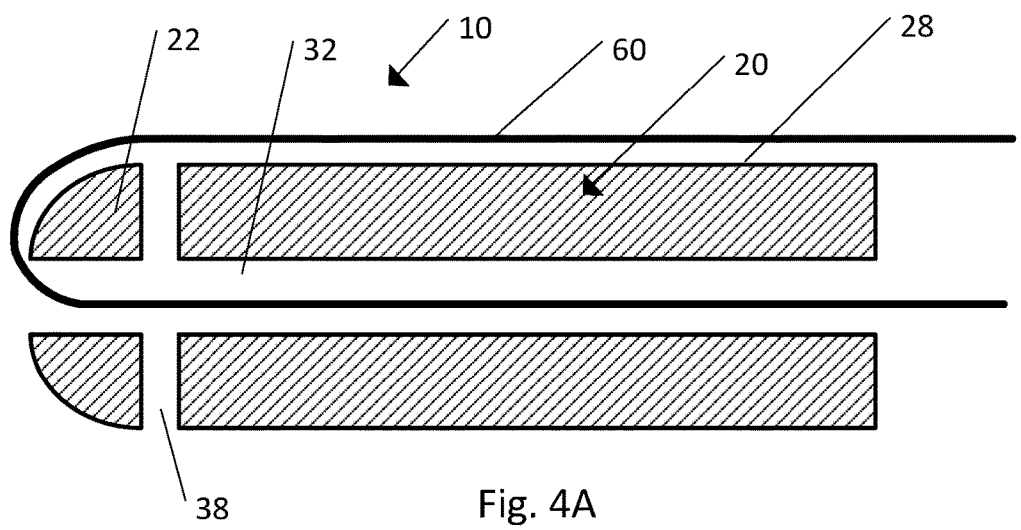
FIG. 4A is a cross-section view of the body and the strand illustrated in FIG. 1B.

Referring to FIG. 4A, in one embodiment the implant 10 includes the body 20 and the strand 60. The implant 10 as shown is in an assembled configuration ready for implantation. The strand 60 has been positioned relative to the body 20 such that the strand 60 is partially disposed within the cannula 32 of the body 20 and partially disposed outside of the body 20, adjacent to (for example abutting) the outer surface 28. As shown, the strand 60 passes through the cannula 32 at the distal end 22 (the distal end 22 shown including a locking aperture 38) such that the strand 60 is partially disposed within the cannula 32 and partially disposed outside the body 20 adjacent the outer surface 28. In this embodiment the implant 10 does not include a strand retention mechanism 70. Although the strand 60 is shown passing through the cannula 32 of the body 20 once, in another embodiment the strand 60 can be looped through the cannula 32 around the outer surface 28 of the body 20 and back through the cannula 32 more than once, increasing the area of the implant 10 that has active agent on it.

Figure 4B:
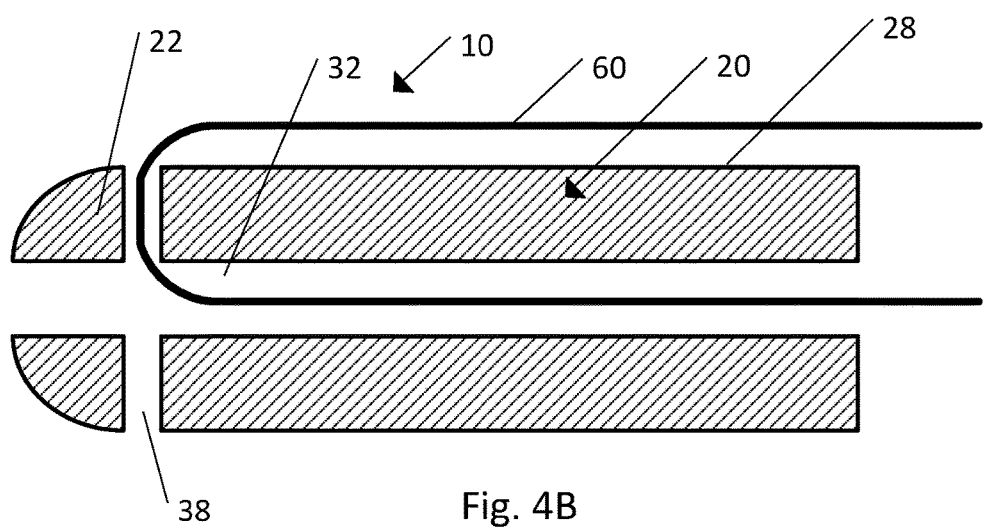
FIG. 4B is a cross-section view of the body and the strand illustrated in FIG. 1B according to another embodiment.

Referring to FIG. 4B, the strand 60 is partially disposed within the cannula 32 of the body 20 and partially disposed outside of the body 20, adjacent to the outer surface 28, similarly to FIG. 4A as described above. However, as shown in the illustrated embodiment, the strand 60 passes through the locking aperture 38 to transition from inside the cannula 32 to outside the body 20. In another embodiment the strand 60 can be passed through any apertures or holes in the body 20 to position the strand 60 as desired relative to the body 20. Typically, the strand extends along the outer surface of the body in a direction substantially parallel with the central axis, but the strand may also extend along the outer surface of the body in other directions.

Figure 4C:
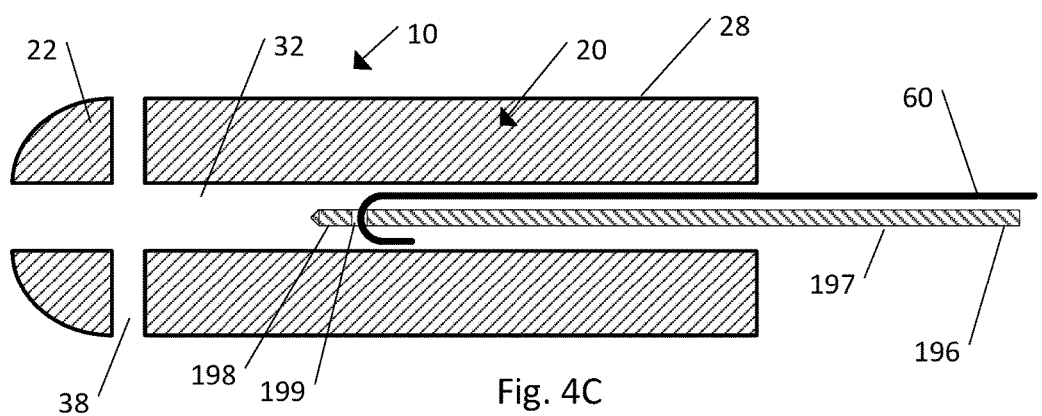
FIG. 4C is a cross-section view of the body and the strand illustrated in FIG. 1B and an insertion tool according to one embodiment.
Figure 4D:
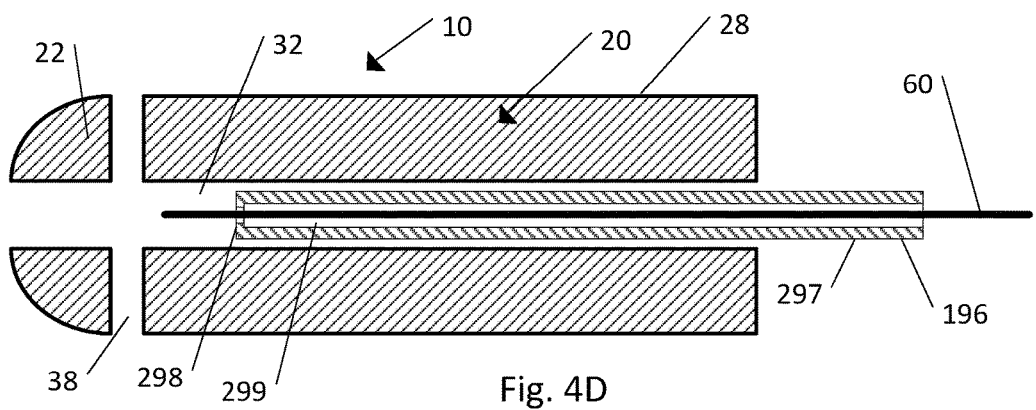
FIG. 4D is a cross-section view of the body and the strand illustrated in FIG. 1B and an insertion tool according to another embodiment.
Figure 4E:
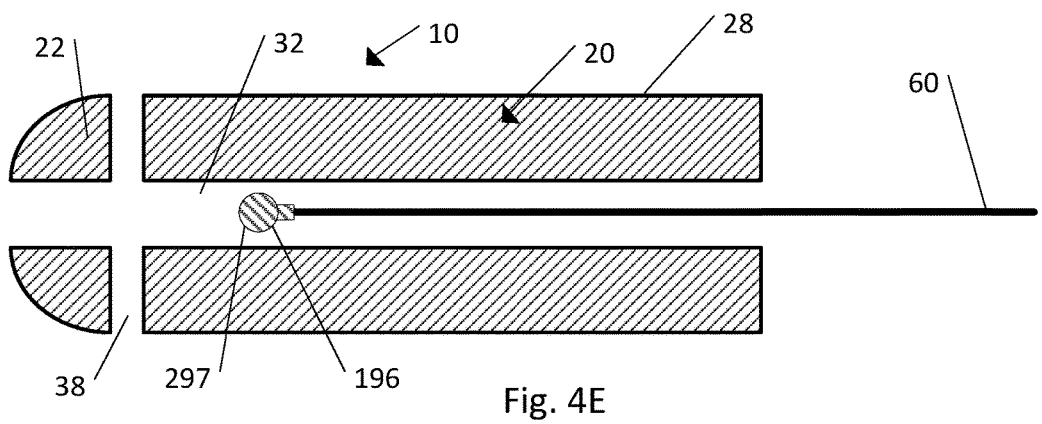
FIG. 4E is a cross-section view of the body and the strand illustrated in FIG. 1B and an insertion tool according to another embodiment.

Referring to FIGS. 4C-4E, an insertion tool 196 can be used to thread the strand 60 through the cannula 32 of the body 20. As shown in FIG. 4C the insertion tool 196 includes a needle-like body 197. The needle-like body 197 can include a lead end 198 and an eyelet 199, the eyelet 199 being disposed near the lead end 198 and configured to receive and retain the strand 60 during insertion of the strand 60 into the cannula 32 of the body 20. In use, the strand 60 is secured within the eyelet 199 of the needle-like body 197. The needle-like body 197 is then passed into and through the cannula 32 in a direction from the proximal end 24 toward the distal end 22. Once the strand 60 has passed through the distal end 22 the strand 60 can be removed from the eyelet 199 and the needle-like body 197 can then be withdrawn back through the cannula 32 in a direction from the distal end 22 toward the proximal end 24.

As shown in FIG. 4D, the insertion tool 196 can include a rod-like body 297. The rod-like body 297 defines a lead end 298 and inner bore 299. The strand 60 is secured to the lead end 298 of the insertion tool 297 and the inner bore 299 encloses at least a portion of the strand 60 during insertion through the cannula 32. The rod-like body 297 is passed into and through the cannula 32 in a direction from the proximal end 24 toward the distal end 22. Once the strand 60 has passed through the distal end 22 the strand 60 can be detached from the lead end 298 and the rod-like body 297 can then be withdrawn back through the cannula 32 in a direction from the distal end 22 toward the proximal end 24 leaving the strand 60 threaded through the length of the cannula 32.

As shown in FIG. 4E, the insertion tool 196 can include a weight 297 attached to the strand 60. The weight 297 can be any shape that fits within the cannula 32. In use the strand 60 can be attached to the weight 297, for instance by knotting the strand 60 to the weight 297. The body 20 can be oriented vertically such that the proximal end 24 faces up and away from the ground and the distal end 22 faces down and toward the ground. The weight is then passed into the cannula 32 at the proximal end 24 and gravity fed toward the distal end 22. Once the weight 297 and the strand 60 have passed through the distal end 22 of the body 20 the weight 297 can be removed from the strand 60. In another embodiment the body 20 can be oriented vertically such that the distal end 22 faces up and away from the ground and the proximal end 24 faces down and toward the ground. The weight is passed into the cannula 32 at the distal end 24 and gravity fed toward the proximal end 22.

Figure 4F:
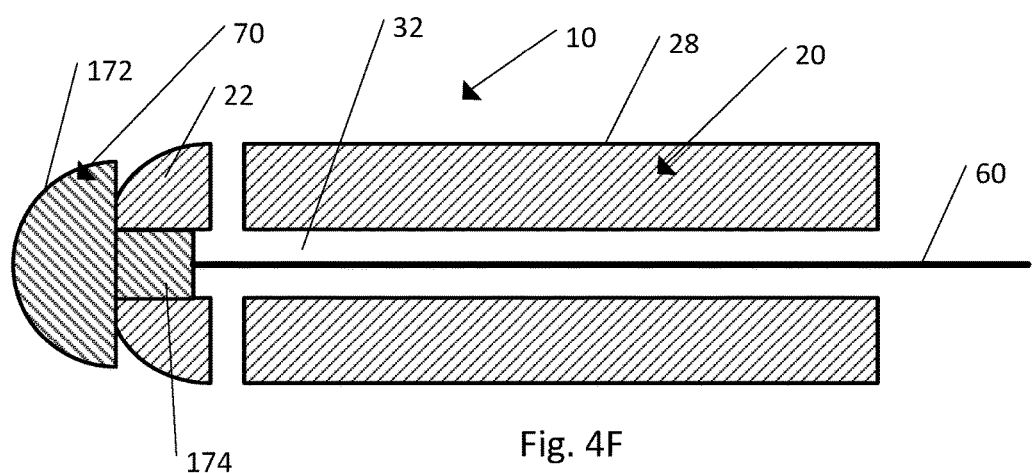
FIG. 4F is a cross-section view of the body, the strand, and the strand retention mechanism illustrated in FIG. 1B, according to one embodiment.
Figure 4G:
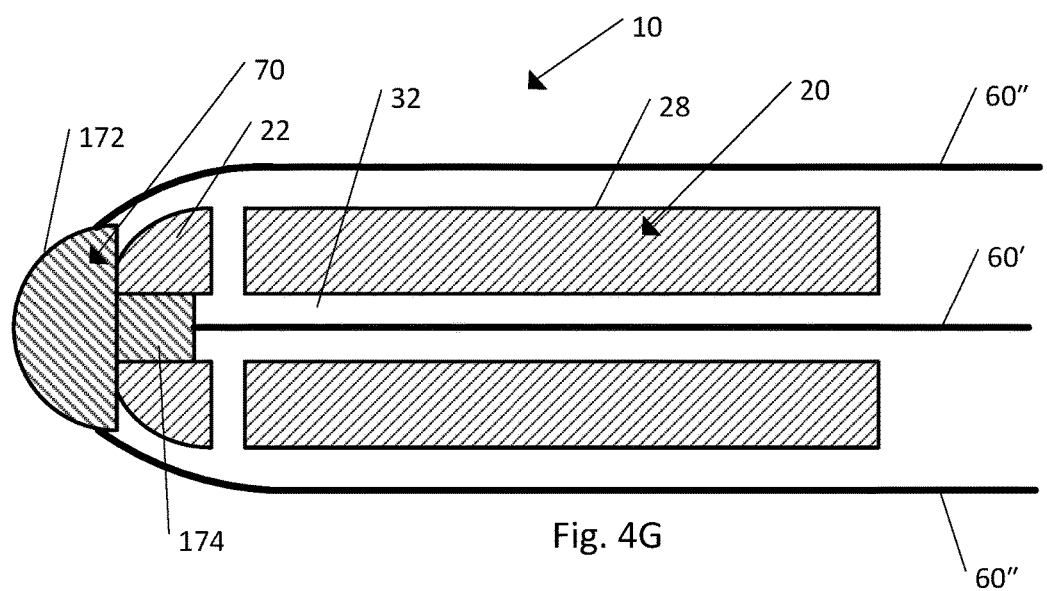
FIG. 4G is a cross-section view of the body, the strand, and the strand retention mechanism illustrated in FIG. 1B, according to another embodiment.

Referring to FIGS. 4F and 4G, in another embodiment the implant 10 includes the body 20, the strand 60, and the strand retention mechanism 70 (including the cap 172). The implant 10 is shown in an assembled configuration ready for implantation. The shaft 174 of the cap 172 has been positioned within the cannula 32 at the distal end 22 of the body 20, such that the cap 172 and the body 20 are secured relative to one another. In one embodiment the strand 60 can be secured to the shaft 174 of the cap 172 such that the strand 60 is positioned entirely within the cannula 32 of the body 20. In another embodiment the strand 60 can be secured to the tip 176 of the cap 172 such that the entire strand 60 is positioned outside the cannula 20 and adjacent to the outer surface 28 of the body 20 (not shown). In another embodiment the implant 10 can include multiple strands 60 (referred to herein as first strand 60' and second strand 60"). One or more first strands 60' can be secured to the shaft 174 of the cap 172 such that the first strands 60' are positioned entirely within the cannula 32 of the body 20. Additionally, one or more second strands 60" can be secured to the tip 176 of the cap 172 such that the second strands 60" are positioned entirely outside the cannula 20 and adjacent to the outer surface 28 of the body 20. In this embodiment the strand retention mechanism 70 is not shown as including a ring member 82, but a ring member 82 could be included.

Figure 4H:
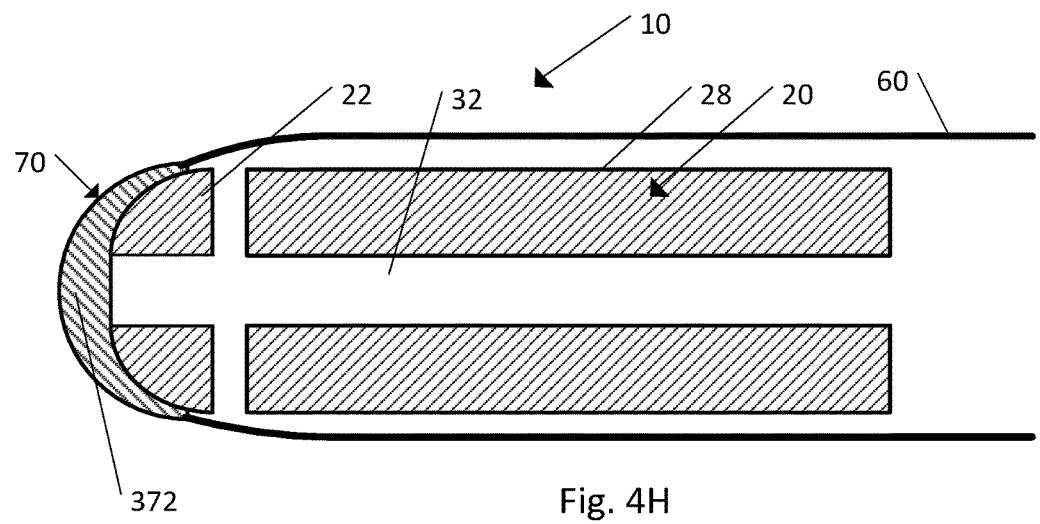
FIG. 4H is a cross-section view of the body, the strand, and the strand retention mechanism illustrated in FIG. 1B, according to another embodiment.

Referring to FIG. 4H, the implant as shown includes the body 20, the strand 60, and the strand retention mechanism 70 (including the cap 372). The implant 10 is shown in an assembled configuration ready for implantation. The cap 372 is configured to fit over the outer surface 28 at the distal end 22 of the body 20. The cap 372 fits over the outer surface 28 at the distal end 22 of the body 20 like a sleeve and is positioned entirely outside of the body 20. The cap 372 can be constructed of an elastic or resilient material such that the cap 372 stretches as it is fit over the outer surface 28 at the distal end 22 of the body 20 and the resilient property of the cap 372 holds the cap 372 in place relative to the body 20. As shown, the strand 60 is secured to the cap 372 such that each of the strands 60 is positioned entirely outside of the cannula 20 and adjacent to the outer surface 28 of the body 20. In this embodiment the strand retention mechanism 70 is not shown as including a ring member 82, but a ring member 82 could be included.

Figure 4I:
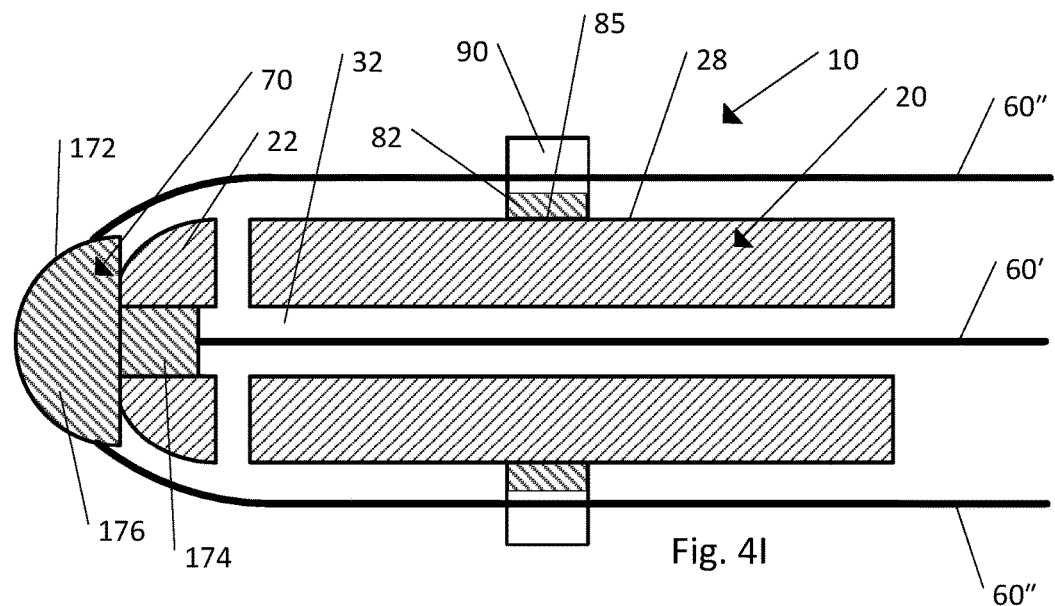
FIG. 4I is a cross-section view of the body, the strand, and the strand retention mechanism illustrated in FIG. 1B, according to another embodiment.

Referring to FIG. 4I, in another embodiment the implant 10 includes the body 20, the strand 60, and the strand retention mechanism 70 (including the cap 172 and the ring member 82). The implant 10 is shown in an assembled configuration ready for implantation. The shaft 174 of the cap 172 has been positioned within the cannula 32 at the distal end 22 of the body 20, such that the cap 172 and the body 20 are secured relative to one another. The body 20 has been positioned within the ring member 82 such that the inner surface 85 of the ring member 82 is in slidable contact with the outer surface 28 of the body 20. In one embodiment the strand 60 can be secured to the shaft 174 of the cap 172 such that the strand 60 is positioned entirely within the cannula 32 of the body 20. In another embodiment the strand 60 can be secured to the tip 176 of the cap 172 such that the entire strand 60 is positioned outside the cannula 20 and adjacent to the outer surface 28 of the body 20. In another embodiment the implant 10 can include multiple strands 60 (referred to herein as first strand 60' and second strand 60"). One or more first strands 60' can be secured to the shaft 174 of the cap 172 such that the first strands 60' are positioned entirely within the cannula 32 of the body 20. Additionally, one or more second strands 60" can be secured to the tip 176 of the cap 172 such that the second strands 60" are positioned entirely outside the cannula 20 and adjacent to the outer surface 28 of the body 20. As shown in the illustrated embodiment, the implant 10 includes both the first strand 60' and second strand 60". In another embodiment the implant 10 can include one or more second strands 60" (disposed outside the cannula 32) and none of the first strands 60' (disposed inside the cannula 32). In yet another embodiment the implant 10 can include one or more of the first strands 60' (disposed inside the cannula 32) and none of the second strands 60" (disposed outside the cannula 32).

The second strands 60" can be slidably received by the strand securing element 90 (not shown) of the ring member 82 such that the second strands 60" are held in a desired spaced relationship relative to one another. In one embodiment the spaced relationship can include the second strands 60" oriented parallel to each other and being spaced apart radially about the outer surface 28 of the body 20. For example, the implant 10 can include four second strands 60" each spaced 90° apart about the outer surface 28. Alternatively, the second strands 60" can have non-uniform spacing. In another embodiment the spaced relationship can include the second strands 60" being wound around the outer surface 28 of the body 20 such that the second strands 60" are either substantially parallel to each other or alternatively such that the second strands 60" crisscross with each other.

Figure 4J:
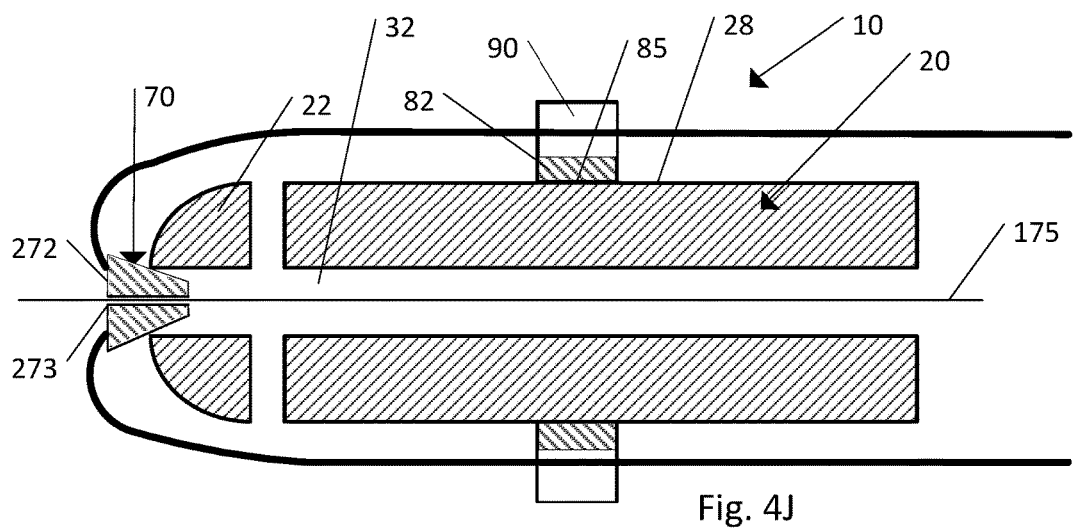
FIG. 4J is a cross-section view of the body, strand, and the strand retention mechanism illustrated in FIG. 1B according to another embodiment.

Referring to FIG. 4J, in another embodiment the implant 10 includes the body 20, the strand 60, and the strand retention mechanism 70 (including the cap 272 and the ring member 82). As shown in the illustrated embodiment, the cap 272 can include a longitudinal bore 273 that extends through the cap 272 such that a passageway is created through the cap 272. During implantation of the implant 10, a K-wire 175 or other guidance mechanism can be passed through the longitudinal bore 273 to aid in implantation of the implant 10. The cap 272 shown in FIGS. 4B-4D can also include a longitudinal bore similar to the longitudinal bore 273 that is configured to receive a K-wire or other guidance mechanism to aid in the implantation of the implant 10.

Figure 4K:
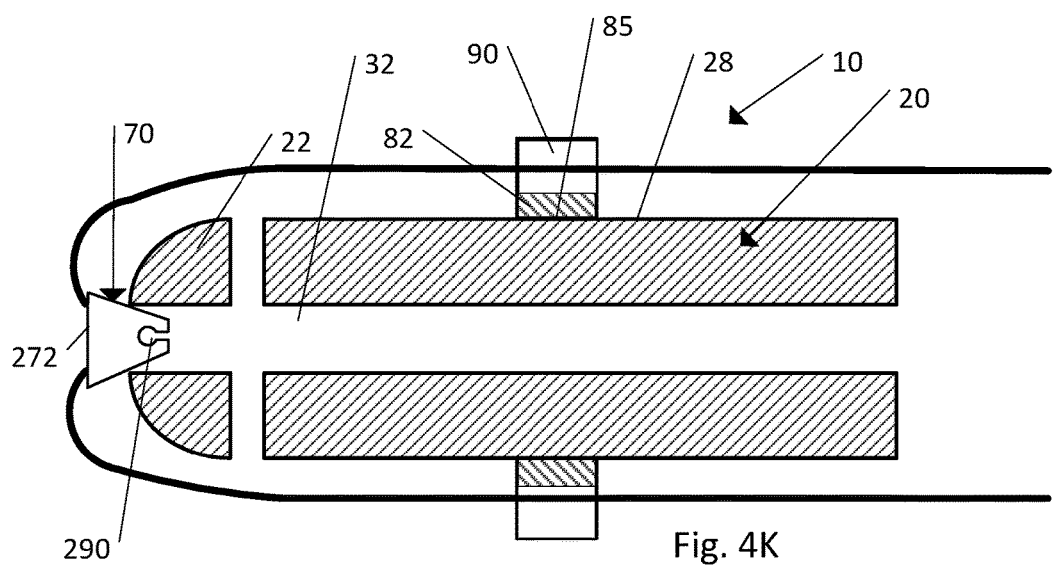
FIG. 4K is a cross-section view of the body, strand, and the strand retention mechanism illustrated in FIG. 1B according to another embodiment.
Figure 4L:
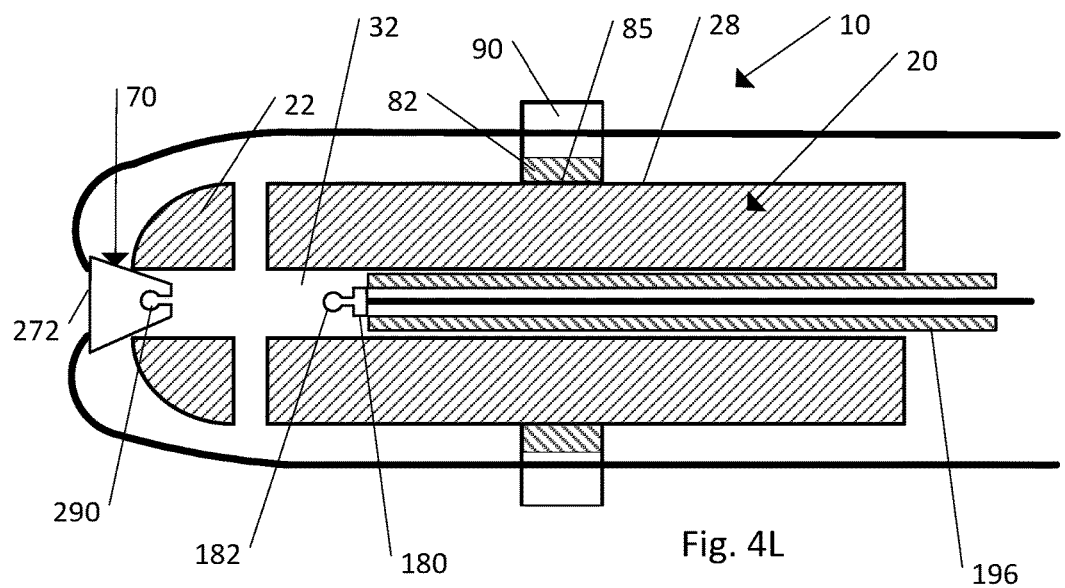
FIG. 4L is a cross-section view of the body, strand, and the strand retention mechanism illustrated in FIG. 1B according to another embodiment.
Figure 4M:
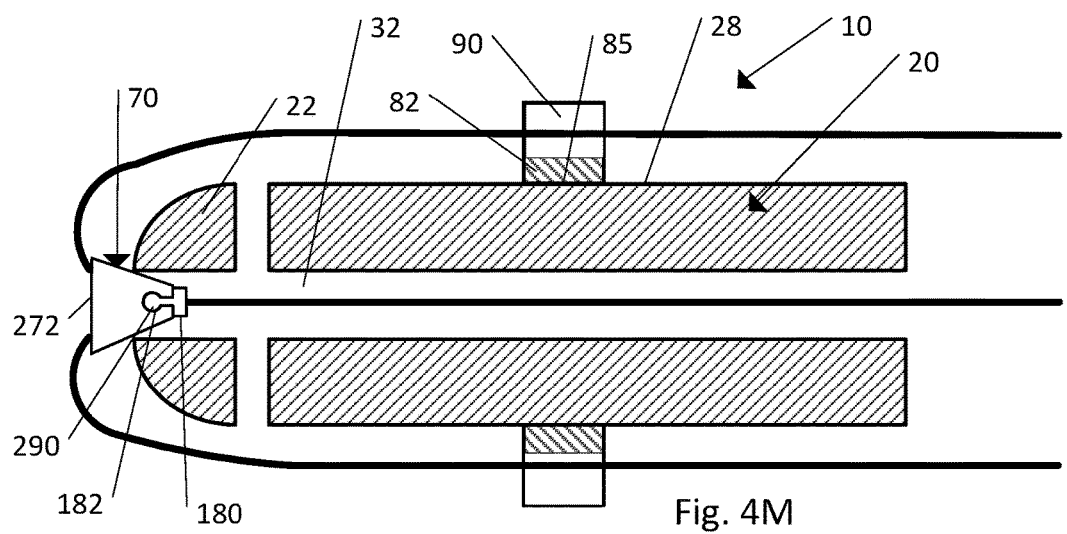
FIG. 4M is a cross-section view of the body, strand, and the strand retention mechanism illustrated in FIG. 1B according to another embodiment.

Referring to FIGS. 4K-4M, still another embodiment of the implant 10 includes the body 20, the strand 60, and the strand retention mechanism 70 (including the cap 272 and optionally the ring member 82). As shown in the illustrated embodiment, a connector 180 with an attached strand 60 can be inserted through the cannula 32 of the body 20 and secured to the cap 272. The cap 272, as shown, includes a connector receiving recess 290. The connector receiving recess 290 is configured to secure the connector 180 relative to the cap 272. The connector 180 defines a leading end 182 with a shape and the connector receiving recess 290 defines a shape that corresponds to the shape of the connector 180. For example, as shown, the shape of the leading end 182 is rounded or ball-shaped and matches the shape of the connector receiving recess 290. In use, the cap 272 is secured to the distal end 22 of the body 20. Then the connector 180 attached to an insertion tool 196 is inserted along the cannula 32 of the body 20. The insertion tool 196 is advanced toward the distal end 22 until the leading end 182 of the connector 180 is received within the corresponding shape of the connector receiving recess 290. As shown the leading end 182 and the connector receiving recess 290 can have corresponding shapes such that the leading end 182 snap fits into the connector receiving recess 290. The insertion tool 196 can then be withdrawn leaving the connector 180 secured to the cap 272 with the strand 60 disposed within the cannula 32 of the body 20. The caps 172 and 372 shown in FIGS. 4F-4I can also include a connector receiving recess similar to the connector receiving recess 290 that is configured to receive a leading end of a connector as described above.

Figure 5A:
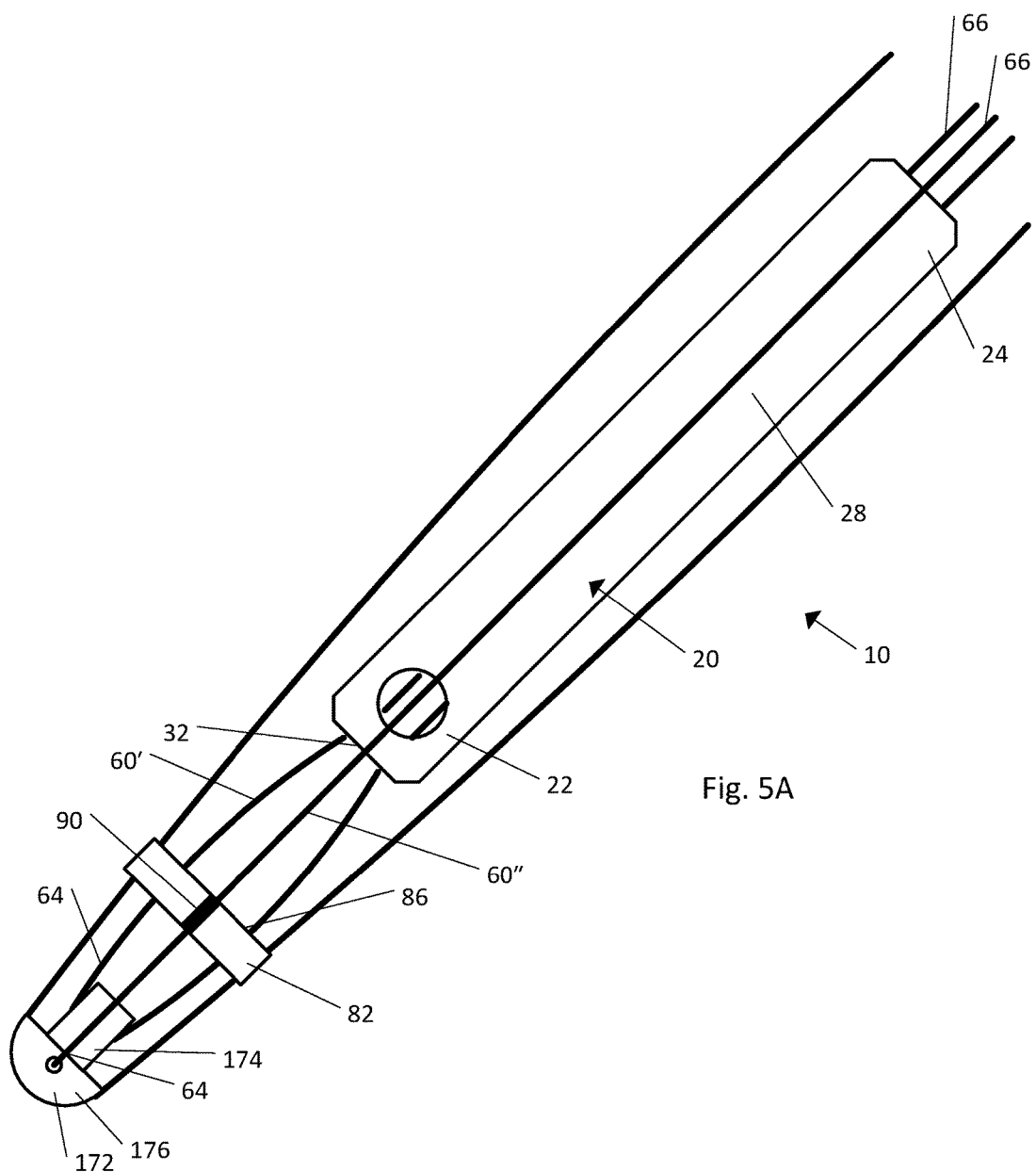
FIG. 5A is a side elevation view of the implant illustrated in FIG. 1B in an unassembled configuration.

Referring to FIG. 5A, the implant 10 can include an unassembled configuration. The one or more strands 60 include a first end 64 and a second end 66. The first end 64 of the first strands 60' attach to the shaft 74 of the cap 72. The second end 66 of the first strands 60' pass through the bore 86 of the ring member 82, pass into the cannula 32 of the body 20 at the distal end 22, and pass out through the proximal end 24. The first end 64 of the second strands 60" attach to the tip 76 of the cap 72. The second end 66 of the second strands 60" pass through the strand securing element 90 of the ring member 82 and pass adjacent the outer surface 28 of the body 20.

Figure 5B:
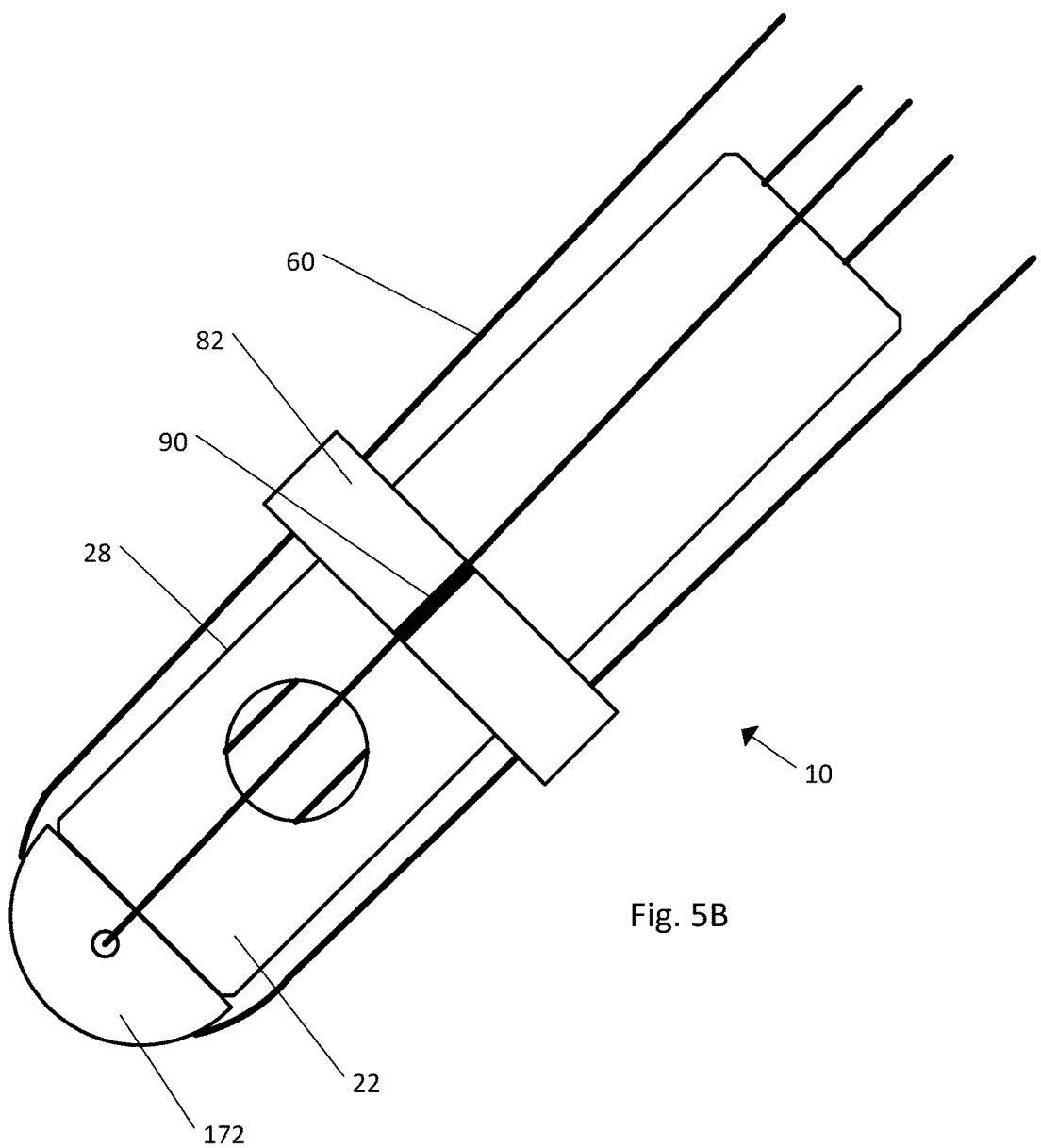
FIG. 5B is a side elevation view of the implant illustrated in FIG. 1B in an assembled configuration.

Referring to FIG. 5B, the implant 10 can include an assembled configuration. The distal end 22 of the body 20 receives the cap 72 and the outer surface 28 receives the ring member 82. Just prior to implantation the ring member 82 can be positioned adjacent the distal end 22 and the strands 60 are pulled taut and slidably received within the strand securing element 90 of the ring member 82.

Figure 6D:
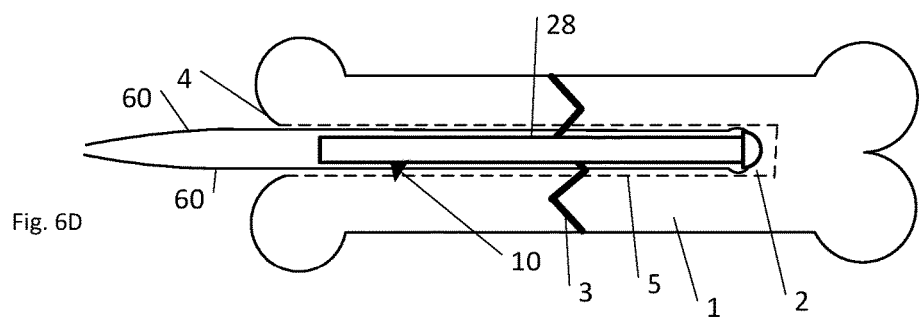
FIG. 6D is a side elevation view of another step of the insertion of the implant illustrated in FIG. 1B into a bone.
Figure 6C:
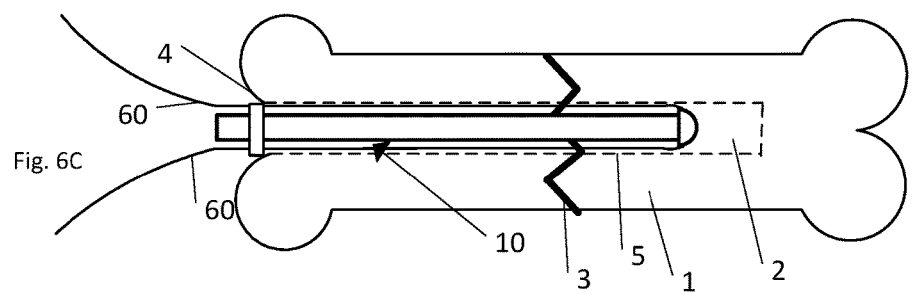
FIG. 6C is a side elevation view of another step of the insertion of the implant illustrated in FIG. 1B into the bone.
Figure 6B:
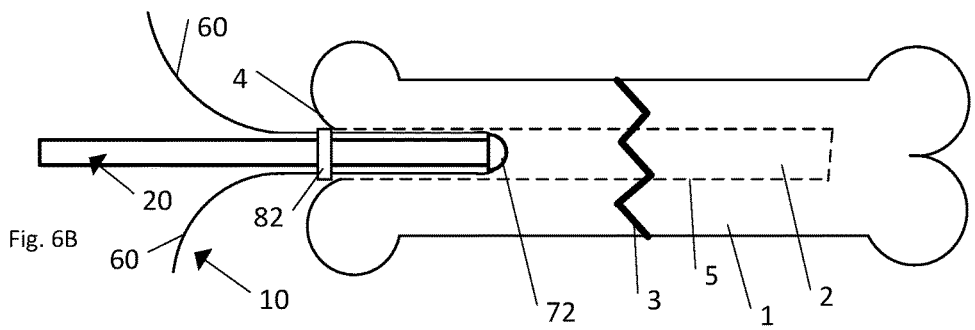
FIG. 6B is a side elevation view of another step of the insertion of the implant illustrated in FIG. 1B into the bone.
Figure 6A:
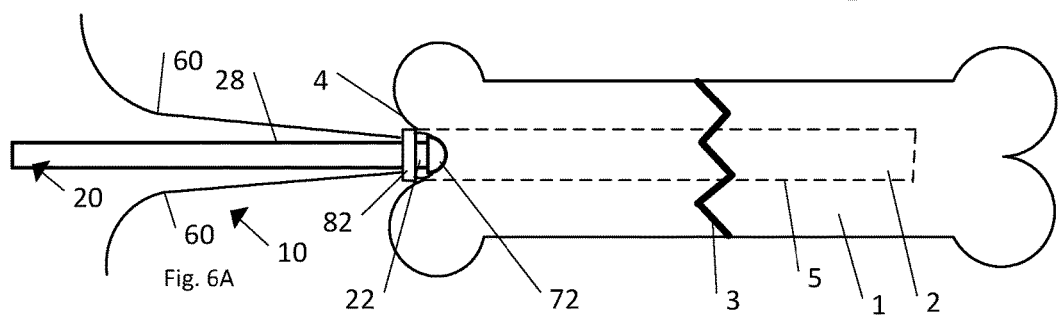
FIG. 6A is a side elevation view of one step of the insertion of the implant illustrated in FIG. 1B into a bone.

Referring to FIG. 6A-6D, a method for treating a fractured bone 1 includes inserting the implant 10 into the medullary cavity 2 as described in detail below. As shown in FIG. 6A the implant 10 is inserted into the medullary cavity 2 at an insertion site 4 such that the cap 72 leads the implant 10 during insertion. The ring member 82, which is positioned about the outer surface 28 of the body 20 at the distal end 22 contacts the exterior of the bone 1 at the insertion site 4. The ring member 82 is configured such that it will abut the exterior of the bone 1 at the insertion site 4, but not enter the medullary cavity 2. As shown in FIG. 6B the body 20 and the cap 72 of the implant 10 have been advanced within the medullary cavity 2 toward the fracture 3. The ring member 82 remains in its earlier position abutting the exterior of the bone 1 at the insertion site 4. As the cap 72 and body 20 advances within the medullary cavity 2, the strands 60, which are secured to the cap 72, advance into the medullary cavity 2 as well. As the strands 60 advance into the medullary cavity 2 along with the cap 72, the strands 60 slide through the strand retention element 90 (not shown) of the ring member 82 while remaining in a desired spaced relationship throughout the insertion of the implant 10. As shown in FIG. 6C the implant 10 has advanced within the medullary cavity 2 such that the body 20 is partially located on both sides of the fracture 3. The strands 60 continue to advance with the cap 72 while the ring member 82 maintains the desired spaced relationship of the strands 60 relative to each other. As shown in FIG. 6D the implant 10 has been fully inserted such that the entire body 20 is positioned within the medullary cavity 2. The body 20 is partially located on both sides of the fracture 3. The ring member 82 has been removed from contact with the outer surface 28 of the body 20. The strands 60 can be tied together or knotted and any excess length can be cut off.

During the insertion process the cap 72 and the strands 60 will be subjected to high shearing forces and thus are preferably configured to withstand those high shearing forces. In one embodiment the body 20 is configured such that the strands 60 are in contact with walls 5 that define the medullary cavity 2, and the strands 60 are wedged between the walls 5 of the medullary cavity 2 and the outer surface 28 of the body 20. In other words, the strands 60 may be positioned on the outer surface 28 of the body 20 that, during implantation, typically contact or may contact the walls 5 of medullary cavity 2. The positioning of the strands 60, in this embodiment, outside of the body 20 subjects the strands 60 to increased shearing forces during insertion of the implant 10 that the strands 60 are typically manufactured and configured to withstand. This method of treatment enables more precise positioning of strands 60 and thus more precise delivery of the active agent that the strands 60 are loaded with.

For example, the strands can be manufactured and configured to move or slide against the walls 5 of the medullary cavity 2 without sustaining damage or deterioration during implantation. Accordingly, in one embodiment, a standard intramedullary nail with a cannula can be used as the body 20 of the implant without the need to alter the surface of the intramedullary nail to incorporate a strand loaded with active agent or otherwise protect the strand from shearing forces. In one embodiment, a strand, such as a bioabsorbable suture, may be axially oriented (drawn) to provide increased tensile strength. The drawn filament may be coated by a dip-coating process with a bioabsorbable polymer containing particles of active agent, such as gentamicin sulfate. The particle of active agent can be suspended in the polymer or dissolved in the coating solution, such that the coating is tenaciously bound to the surface of the filament. The filament and/or coating typically has sufficient strength to be positioned on the outer surface of an intramedullary nail and inserted into the medullary canal of a bone without damaging the suture or stripping off the coating.

Referring to FIGS. 7A-7L, a variety of strands 60 can be loaded with active agent 62 in a variety of ways such that the strand 60 retains the active agent 62 during implantation of the strand 60. For example, the strand 60 could be spray coated with a solution that includes a drug-polymer-solvent mixture. Additionally, filaments can be extruded with the drug so that a secondary coating process is not necessary. Further, the filaments can be electrospun.

The active agent 62 can be used to increase the effectiveness of treatment of a fractured bone by reducing the risk of or preventing infection, promoting healing, etc. The active agent can include particles 63 (of gentamicin or other antibiotics, in addition to growth factors, analgesics, and anti-inflammatory compounds, for example) and a coating 65. The strand and/or coating material may include an additive to make the strand and/or coating material more water permeable or swellable, for the purpose of increasing the drug release rate from the strand and/or coating.

The coating can include a polymer, such as polyurethanes, that can be bioabsorbable or biostable (non-absorbable). Additional examples of bioabsorbable polymers can include polylactic acid (PLA), polyglycolic acid (PGA), polycaprolactone (PCL), polymethylene carbonate (PMC), polyethylene glycol (PEG) or copolymers of these. Alternately, the coating can be made of some material other than a polymer such as calcium stearate, magnesium stearate, dextran, collagen, gelatin, polypeptides, proteins, or carbohydrates. In one embodiment a layer of the active agent 62 can have a thickness of from about 0.01 mm to about 0.07 mm.

Figure 7A:
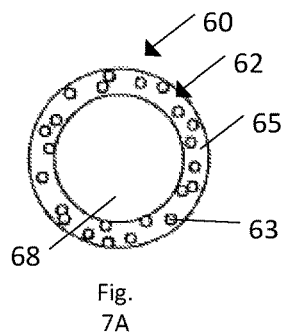
FIG. 7A is a front cross-section view of the strand illustrated in FIG. 1B according to one embodiment.
Figure 7B:
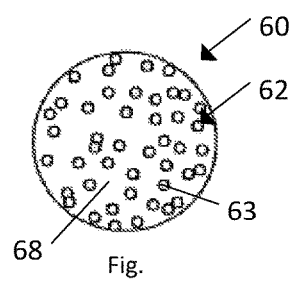
FIG. 7B is a front cross-section view of the strand illustrated in FIG. 1B according to another embodiment.
Figure 7C:
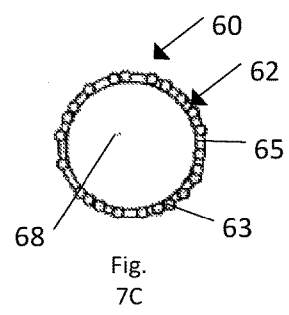
FIG. 7C is a front cross-section view of the strand illustrated in FIG. 1B according to another embodiment.

As shown in FIG. 7A the strand 60 can include a core 68 that is a monofilament. The particles 63 are disposed within the coating 65. The coating 65 is layered around the core 68, and the coating 65 is thicker than the diameter of the particles 63. As shown in FIG. 7B the strand 60 can include a core 68 that is a monofilament. The particles 63 are distributed throughout the core 68. The particles 63 can be distributed evenly or unevenly. In this embodiment the active agent 62 can lack the coating 65. As shown in FIG. 7C the strand 60 can include a core 68 that is a monofilament. The particles 63 are disposed within the coating 65. The coating 65 is layered around the core 68, and the coating 65 is thinner than the diameter of the particles 63, such that more of the particles 63 are exposed.

Figure 7D:
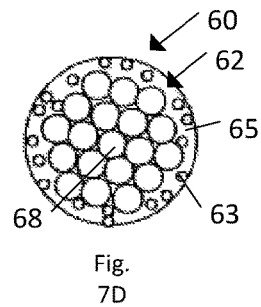
FIG. 7D is a front cross-section view of the strand illustrated in FIG. 1B according to another embodiment.
Figure 7E:
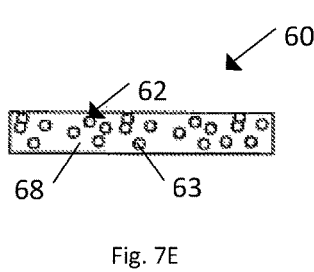
FIG. 7E is a side cross-section view of the strand illustrated in FIG. 1B according to another embodiment.
Figure 7F:
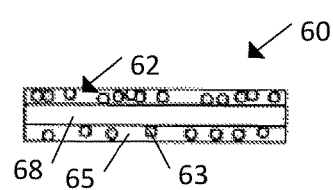
FIG. 7F is a side cross-section view of the strand illustrated in FIG. 1B according to another embodiment.

As shown in FIG. 7D the strand 60 can include a core 68 that is multifilament. The particles 63 are disposed within the coating 65. The coating 65 is layered around the core 68, and the coating 65 is thicker than the diameter of the particles 63. As shown in FIG. 7E the strand 60 can include a core 68 that is a flat strip (or ribbon). In one embodiment core 68 is made from a polymer material. The particles 63 are distributed throughout the core 68. The particles 63 can be distributed evenly or unevenly. As shown in FIG. 7F the strand 60 can include a core 68 that is a flat strip (or ribbon). In one embodiment the core 68 is made from a polymer material. The core 68 as shown can be solid polymer with the coating 65 containing the particles 63 disposed on either side of the core 68.

Figure 7G:
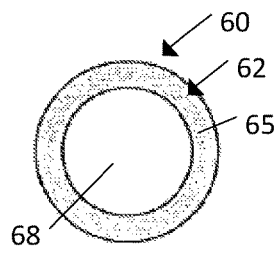
FIG. 7G is a front cross-section view of the strand illustrated in FIG. 1B according to another embodiment.
Figure 7H:
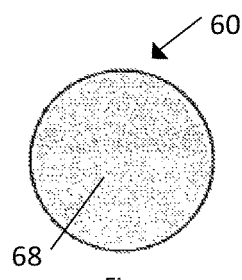
FIG. 7H is a front cross-section view of the strand illustrated in FIG. 1B according to another embodiment.
Figure 7I:
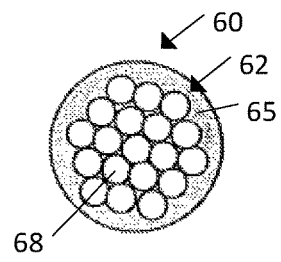
FIG. 7I is a front cross-section view of the strand illustrated in FIG. 1B according to another embodiment.

As shown in FIG. 7G the strand 60 can include a core 68 that is a monofilament. The coating 65 is layered about the core 68 and the coating 65 includes dissolved antibiotic. The active agent 62 can lack particles 63 in this embodiment. As shown in FIG. 7H the strand 60 can include a core 68 that is a monofilament. The active agent 62 (not shown) includes dissolved antibiotic distributed through the core 68. The dissolved antibiotic can be distributed evenly or unevenly. The active agent 62 can lack the particles 63 and the coating 65 in this embodiment. As shown in FIG. 7I the strand 60 can include a core 68 that is multifilament. The coating 65 is layered about the core 68 and the coating 65 includes dissolved antibiotic. The active agent 62 can lack particles 63 in this embodiment.

Figure 7J:
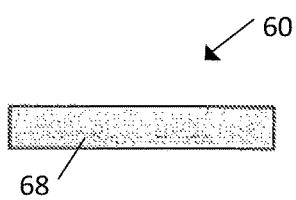
FIG. 7J is a side cross-section view of the strand illustrated in FIG. 1B according to another embodiment.
Figure 7K:
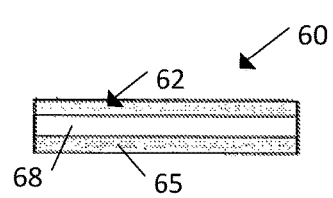
FIG. 7K is a side cross-section view of the strand illustrated in FIG. 1B according to another embodiment.
Figure 7L:
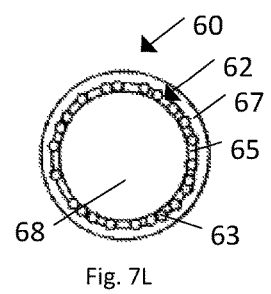
FIG. 7L is a front cross-section view of the strand illustrated in FIG. 1B according to another embodiment

As shown in FIG. 7J the strand 60 can include a core 68 that is a flat strip (or ribbon). In one embodiment the core 68 is made from a polymer material. The active agent 62 (not shown) includes dissolved antibiotic distributed through the core 68. The dissolved antibiotic can be distributed evenly or unevenly. The active agent 62 can lack the particles 63 and the coating 65 in this embodiment. As shown in FIG. 7K the strand 60 can include a core 68 that is a flat strip (or ribbon). In one embodiment the core 68 is made from a polymer material. The core 68 as shown can be solid polymer with the coating 65 containing dissolved antibiotic disposed on either side of the core 68. The active agent 62 can lack particles 63 in this embodiment. As shown in FIG. 7L the strand 60 can include a core 68 that is a monofilament. The particles 63 are disposed within the coating 65. The coating 65 is layered around the core 68, and the coating 65 is thinner than the diameter of the particles 63. As shown the active agent can include a barrier coating 67, for example formed by a second layer of polymer, such that a barrier protects the particles 63 from exposure.

Referring to FIGS. 8A-8D, an implantable body can also include a strand 60 secured to other types of implants, such as a bone plate 500. The bone plate 500 includes an outer surface, that can include a bottom bone-contacting surface 501, an opposed top surface 503, and an outer periphery 513. The bone plate 500 also includes opposed ends, for instance a distal end 505 and a proximal end 507. The bone plate 500 further includes a body 509 that extends from the distal end 505 to the proximal end 507 along a direction parallel to a central axis 511, such that the body 509 defines a length. The body 509 also extends from the bottom surface 501 to the top surface 503 along a direction perpendicular to the central axis 211, such that the body 509 defines a thickness. The body 509 further defines at least one aperture, for example at least one fastener hole 502, 504, 506, 508, 510 that extends from the bottom surface 501 to the top surface 503. Each of the fastener holes 502 is typically configured to receive a bone fastener, for instance a non-locking bone screw that secures the bone plate 500 to an underlying bone. The bone plate 500 can include one or more of a single non-locking screw hole 502, a multi locking and non-locking screw hole 504, a multi locking screw hole 506, a multi non-locking screw hole 508, a single locking screw hole 510 or any combination thereof. In general, any of the fastener holes 502, 504, 506, 508, 510 may be used whether or not the fastener holes 502, 504, 506, 508, 510 ultimately receive a screw or fastener during application. In another embodiment the strand can be attached to the bone plate without the use of any fastener holes 502, 504, 506, 508, 510, for instance by using an adhesive to secure the strand 60 to either the bottom surface 501 or the top surface 503. In other embodiments (not shown), an insert or cap similar to those described herein may be used as the strand retention mechanism and configured to fit within or over one or more of the fastener holes to anchor the strand to the bone plate.

As shown in FIG. 8A, the strand 60 can be secured to the bone plate 500 as shown by passing the strand 60 through one of the fastener holes 502, 504, 506, 508, 510 and tying a knot in the strand 60. Once the strand 60 has been looped through one of the fastener holes 502, 504, 506, 508, 510 the remainder of the strand 60 can be positioned along the bottom surface 501 of the bone plate 500. Upon insertion the strand 60 will be positioned between the bone plate 500 and the underlying bone to deliver the active agent loaded on the strand 60 and prevent medical complications. In another embodiment, once the strand 60 has been looped through one of the fastener holes 502, 504, 506, 508, 510 the remainder of the strand 60 can be positioned along the top surface 503 of the bone plate 500. Upon insertion the strand 60 will be positioned between the bone plate 500 and a soft tissue layer to deliver the active agent loaded on the strand 60 and prevent medical complications. In still another embodiment, one or more strands 60 can be positioned on both the bottom surface 501 and the top surface 503. Typically, the strand extends along the outer surface in a direction substantially parallel to the central axis, but the strand may also extend along the outer surface of the body in other directions.

As shown in FIGS. 8B and 8C, in another embodiment the strand 60 can be looped through more than one fastener hole 502, 504, 506, 508, 510, for instance through two holes. The strand can be looped through the fastener holes once or more than once until the desired ratio of active agent loaded strands 60 to bone plate 500 is achieved.

As shown in FIG. 8D, the strand 60 can be attached to the bone plate 500 by looping one or more strands 60 through non-fastener holes 512. The non-fastener holes 512 can be any hole that is not typically used to receive a bone fastener to secure the bone plate 500 to the underlying bone. In one embodiment the non-fastener holes 512 can extend from the bottom surface 501 to the top surface 503 along a direction perpendicular to the central axis 211 such that a passageway is provided through the entire thickness of the bone plate 500. In another embodiment the non-fastener hole 512 can extend from one of the bottom surface 501 or the top surface 503 to the outer periphery 513, such that a passageway is provided through only a portion of the thickness of the bone plate 500.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the claims.

What is claimed:

1. An implant comprising:
a body having a proximal end, a distal end, and a round outer surface extending from the proximal end to the distal end and defining a substantially circular cross-section along a length of the body from the proximal end to the distal end, wherein the substantially circular cross-section defines an outer diameter of the body, wherein the body defines a central axis extending from the proximal end to the distal end and wherein the body further defines at least one aperture; and
a high tensile strand positioned adjacent the body such that at least a portion of the strand extends at least partially along the round outer surface of the body outside the outer diameter in a direction substantially parallel with the central axis, wherein the strand is at least partially disposed within an aperture of the at least one aperture, and wherein the strand is loaded with an active agent;
wherein an aperture of the at least one aperture extends from the outer surface into the body such that the aperture is angularly offset with the central axis.

2. The implant of claim 1, wherein the strand is biodegradable.

3. The implant of claim 1, wherein the strand further includes a coating layer.

4. The implant of claim 3, wherein the active agent is disposed as particles within the coating layer.

5. The implant of claim 3, wherein the active agent is dissolved within the coating layer.

6. The implant of claim 1, wherein the active agent is dissolved within the strand.

7. The implant of claim 1, wherein the active agent is disposed as particles within the strand.

8. The implant of claim 1, wherein the strand includes a monofilament.

9. The implant of claim 1, wherein the strand includes a multifilament.

10. The implant of claim 1, wherein the strand includes at least one ribbon.

11. The implant of claim 1, wherein the active agent includes at least one antibiotic.

12. The implant of claim 11, wherein the at least one antibiotic includes gentamicin.

13. The implant of claim 1, wherein strand comprises one or more strands.

14. The implant of claim 13, wherein the one or more strands are spaced apart from one another radially outside the outer diameter of the body along the outer surface.

15. The implant of claim 1, wherein the strand is in contact with and configured to move or slide against the outer surface of the body during implantation.

16. The implant of claim 1, wherein an aperture of the at least one aperture is configured to receive a bone fastener.

17. The implant of claim 16, wherein the strand is at least partially disposed in the aperture configured to receive a bone fastener.

18. The implant of claim 1, wherein the strand is at least partially disposed within the angularly offset aperture.

19. The implant of claim 1, wherein as the body is implanted to a bone, at least a portion of the strand is in contact with both the outer surface of the body and the bone.

20. The implant of claim 1, wherein the body includes an inner surface that defines a cannula, and wherein the cannula extends in a direction coaxial with the central axis along at least a portion of the implant, and further wherein the strand is at least partially disposed within the cannula of the body.

21. The implant of claim 1, wherein the body is configured as an intramedullary nail.

* * * * *